US008492564B2

(12) United States Patent
Beguin et al.

(10) Patent No.: US 8,492,564 B2
(45) Date of Patent: Jul. 23, 2013

(54) SALVINORIN DERIVATIVES AND USES THEREOF

(75) Inventors: Cecile Beguin, Lexington, MA (US); Justin Stephen Potuzak, Millis, MA (US); Thomas Anthony Munro, Cambridge, MA (US); Katharine K. Duncan, San Diego, CA (US); William A. Carlezon, Lincoln, MA (US); Bruce M. Cohen, Lexington, MA (US); Lee-yuan Liu-Chen, Media, PA (US)

(73) Assignees: The McLean Hospital Corporation, Belmont, MA (US); Temple University School of Medicine, Philadelphia, PA (US)

( * ) Notice: Subject to any disclaimer, the term of this patent is extended or adjusted under 35 U.S.C. 154(b) by 0 days.

(21) Appl. No.: 13/133,824

(22) PCT Filed: Dec. 14, 2009

(86) PCT No.: PCT/US2009/067929
§ 371 (c)(1),
(2), (4) Date: Sep. 29, 2011

(87) PCT Pub. No.: WO2010/075045
PCT Pub. Date: Jul. 1, 2010

(65) Prior Publication Data
US 2012/0010219 A1 Jan. 12, 2012

Related U.S. Application Data

(60) Provisional application No. 61/122,668, filed on Dec. 15, 2008.

(51) Int. Cl.
*C07D 409/00* (2006.01)
*C07D 311/78* (2006.01)
(52) U.S. Cl.
USPC ............................................ 549/60; 549/280

(58) Field of Classification Search
USPC .................................................. 549/60, 280
See application file for complete search history.

(56) References Cited

U.S. PATENT DOCUMENTS

2006/0052439 A1 3/2006 Beguin et al.
2006/0058264 A1 3/2006 Prisinzano
2006/0083679 A1 4/2006 Zjawiony et al.

FOREIGN PATENT DOCUMENTS

WO WO-02/49643 A1 6/2002
WO WO-2005/089745 A1 9/2005

OTHER PUBLICATIONS

Beguin et al. Bioorganic & Medicinal Chemistry (2009), 17(3), 1370-1380.*

Béguin et al., "Differential signaling properties at the kappa opioid receptor of 12-epi-salvinorin A and its analogues," *Bioorg Med Chem Lett.* 22: 1023-1026, 2012.
Béguin et al., "Modification of the furan ring of salvinorin A: identification of a selective partial agonist at the kappa opioid receptor," 17: 1370-1380, Epub Dec. 14, 2008.

Béguin et al., "*N*-Methylacetamide Analog of Salvinorin A: A Highly Potent and Selective κ-Opioid Receptor Agonist with Oral Efficacy," *J. Pharmacol. Exp. Ther*, 324:188-195 (2008).

Béguin et al., "Synthesis and In Vitro Evaluation of Salvinorin A Analogues: Effect of Configuration at C(2) and Substitution at C(18)," *Bioorg. Med. Chem. Lett.* 16:4679-4685 (2006).

Béguin et al., "Synthesis and In Vitro Pharmacological Evaluation of Salvinorin A Analogues Modified at C(2)," *Bioorg. Med. Chem. Lett.* 15:2761-2765 (2005).

Bigham et al., "Divinatorins A-C, New Neoclerodane Diterpenoids from the Controlled Sage *Salvia divinorum*," *J. Nat. Prod.* 66: 1242-1244 (2003).

Bikbulatov et al., "Short synthesis of a novel class of salvinorin A analogs with hemiacetalic structure," *Tetrahedron Lett.* 49: 937-940, 2008.

Butelman et al., "The Plant-Derived Hallucinogen, Salvinorin A, Produces κ-Opioid Agonist-Like Discriminative Effects in Rhesus Monkeys," *Psychopharmacol.* 172:220-224 (2004).

Carlezon et al., "Depressive-Like Effects of the κ-Opioid Receptor Agonist Salvinorin A on Behavior and Neurochemistry in Rats," *J. Pharmacol. Exp. Ther.* 316:440-447 (2006).

Chavkin et al., "Salvinorin A, an Active Component of the Hallucinogenic Sage *Salvia divinorum* Is a Highly Efficacious κ-Opioid Receptor Agonist: Structural and Functional Considerations," *J. Pharmacol. Exp. Ther.* 308: 1197-1203 (2004).

Chupp et al., "Behavior of Benzyl Sulfoxides Toward Acid Chlorides. Useful Departures from the Pummerer Reaction," *J. Org. Chem.* 49:4711-4716 (1984).

Communication from European Patent Application No. 05725639, dated Jul. 3, 2008.

Communication from European Patent Application No. 05725639 enclosing Supplementary Partial European Search Report for European Patent Application No. 05725639, dated Feb. 29, 2008.

Giroud et al., "*Salvia divinorum*: An Hallucinogenic Mint which Might Become a New Recreational Drug in Switzerland," *Forensic Sci. Int.* 112:143-150 (2000).

Harding et al., "Synthetic Studies of Neoclerodane Diterpenes from *Salvia divinorum*: Selective Modification of the Furan Ring," *Bioorg. Med. Chem. Lett.* 16:3170-3174 (2006).

Harding et al., "Synthetic Studies of Neoclerodane Diterpenes from *Salvia divinorum*: Semisynthesis of Salvinicins A and B and Other Chemical Transformations of Salvinorin A," *J. Nat. Prod.* 69:107-112 (2006).

Huang et al., "Comparison of Pharmacological Activities of Buprenorphine and Norbuprenorphine: Norbuprenorphine Is a Potent Opioid Agonist," *J. Pharmacol. Exp. Ther.* 297:688-695 (2001).

International Preliminary Report on Patentability for PCT/US05/08603, dated Sep. 13, 2006.

International Preliminary Report on Patentability for PCT/US09/67929, dated Jun. 21, 2011.

(Continued)

*Primary Examiner* — Nizal Chandrakumar
(74) *Attorney, Agent, or Firm* — Clark & Elbing LLP

(57) ABSTRACT

The invention features salvinorin compositions that are selective for kappa opioid receptors; methods of treating mania by using a selective kappa receptor agonist; and methods of treating mood disorders, such as depressive disorders and manic disorders, using salvinorin compositions.

12 Claims, 5 Drawing Sheets

OTHER PUBLICATIONS

International Search Report for PCT/US05/08603, dated Jul. 11, 2005.

International Search Report for PCT/US09/67929, dated Apr. 14, 2010.

Koreeda et al., "The Absolute Stereochemistry of Salvinorins," *Chem. Lett.* 19:2015-2018 (1990).

Lee et al., "Synthesis and In Vitro Pharmacological Studies of C(4) Modified Salvinorin A Analogues," *Bioorg. Med. Chem. Lett.* 15:4169-4173 (2005).

Lee et al., "Synthesis and In Vitro Pharmacological Studies of New C(2) Modified Salvinorin A Analogues," *Bioorg. Med. Chem. Lett.* 15:3744-3747 (2005).

Ma et al., "Dynorphinergic GABA Neurons Are a Target of Both Typical and Atypical Antipsychotic Drugs in the Nucleus Accumbens Shell, Central Amygdaloid Nucleus and Thalamic Central Medial Nucleus," *Neuroscience* 121:991-998 (2003).

Mague et al., "Antidepressant-Like Effects of κ-Opioid Receptor Antagonists in the Forced Swim Test in Rats," *J. Pharmacol. Exp. Ther.* 305:323-330 (2003).

McCurdy et al., "Studies Directed toward Understanding the Opioid Receptor Recognition of Salvinorin A, a Non-Nitrogenous Natural Product with Kappa Opioid Receptor Selectivity," *2003 Narcotics Research Conference*, Abstract #28, p. 51.

Munro et al., "Studies toward the Pharmacophore of Salvinorin A, A Potent κ Opioid Receptor Agonist," *J. Med. Chem.* 48:345-348 (2005).

Munro and Rizzacasa, "Salvinorins D-F, New Neoclerodane Diterpenoids from *Salvia divinorum*, and an Improved Method for the Isolation of Salvinorin A," *J. Nat. Prod.* 66:703-705 (2003).

Munro et al., "8-*epi*-Salvinorin B: Crystal Structure and Affinity at the κ Opioid Receptor," *Beilstein J. Org. Chem.* 3:1-5 (2007).

Pliakas et al., "Altered Responsiveness to Cocaine and Increased Immobility in the Forced Swim Test Associated with Elevated cAMP Response Element-Binding Protein Expression in Nucleus Accumbens," *J. Neurosci.* 21:7397-7403 (2001).

Pogozheva et al., "Opioid Receptor Three-Dimensional Structures from Distance Geometry Calculations with Hydrogen Bonding Constraints," *Biophys. J.* 75:612-634, 1998.

Roth et al., "Salvinorin A: A Potent Naturally Occurring Non-nitrogenous κ Opioid Selective Agonist," *Proc. Nat. Acad. Sci. U.S.A.* 99:11934-11939 (2002).

Sheffler and Roth, "Salvinorin A: The 'Magic Mint' Hallucinogen Finds a Molecular Target in the Kappa Opioid Receptor," *Trends Pharmacol. Sci.* 24:107-109 (2003).

Siebert, "Localization of Salvinorin A and Related Compounds in Glandular Trichomes of the Psychoactive Sage, *Salvia divinorum*," *Ann. Bot.* 93: 763-771 (2004).

Simpson et al., "Synthetic Studies of Neoclerodane Diterpenes from *Salvia divinorum*: Preparation and Opioid Receptor Activity of Salvinicin Analogues," *J. Med. Chem.* 50:3596-3603 (2007).

Spanagel et al., "Opposing Tonically Active Endogenous Opioid Systems Modulate the Mesolimbic Dopaminergic Pathway," *Proc. Natl. Acad. Sci. U.S.A.* 89:2046-2050, 1992.

Valdés et al., "Divinorin A, a Psychotropic Terpenoid, and Divinorin B from the Hallucinogenic Mexican Mint *Salvia divinorum*," *J. Org. Chem.* 49:4716-4720 (1984).

Valdés et al., "Salvinorin C, a New Neoclerodane Diterpene from a Bioactive Fraction of the Hallucinogenic Mexican Mint *Salvia divinorum*," *Org. Lett.* 3:3935-3937 (2001).

Zdero et al., "*Ent*-Clerodanes and Other Constituents from Bolivian *Baccharis* Species," *Phytochem.* 28:531-542 (1989).

Zhang et al., "Kappa Agonist Salvinorin A Induced Conditioned Place Aversion in C57BL/6J Mice," *2003 Narcotics Research Conference*, Abstract #102, p. 70.

Zhu et al., "Activation of the Cloned Human *Kappa* Opioid Receptor by Agonists Enhances [35S]GTPγS Binding to Membranes: Determination of Potencies and Efficacies of Ligands," *J. Pharmacol. Exp. Ther.* 282:676-684 (1997).

Written Opinion of the International Searching Authority for PCT/US05/08603, dated Jul. 11, 2005.

Written Opinion of the International Searching Authority for PCT/US09/67929, dated Apr. 14, 2010.

\* cited by examiner

SALVINORIN DERIVATIVES AND USES THEREOF

CROSS-REFERENCE TO RELATED APPLICATIONS

This application is the U.S. national stage filing under 35 U.S.C. §371 of international application PCT/US2009/067929, filed Dec. 14, 2009, which claims benefit of the filing date of U.S. Provisional Application No. 61/122,668, filed Dec. 15, 2008.

BACKGROUND OF THE INVENTION

The invention relates to the treatment of depressive disorders and mania.

Stressors that cause symptoms of depression increase the activation of cAMP response element-binding protein (CREB) in the nucleus accumbens. CREB activation results in the activation of the prodynorphin gene, which encodes the opioid peptide dynorphin. Dynorphin is an agonist of the kappa opioid receptors in the brain, and enhances symptoms of depression. It has been shown that kappa receptor antagonists can act as antidepressants by mediating a disinhibition of dopamine release in the nucleus accumbens. See Pliakas et al., *J. Neurosci.* 21:7397 (2001); and Mague et al., *J. Pharmacol. Exp. Ther.* 305:323 (2003). It has been shown that antimanic/antipsychotic drugs increase the activity of dynorphinergic neurons, which have their effects through kappa receptors (Ma et al., *Neuroscience* 121:991 (2003).

The diterpene salvinorin A, derived from *Salvia divinorum*, has recently been shown to be a high affinity and selective kappa opioid receptor agonist. See Roth et al., *Proc. Natl. Acad. Sci. USA* 99: 11934 (2002); and Butelman et al., *Psychopharmacology* 172:220 (2004).

New compounds which are highly selective for kappa opioid receptors over mu and delta opioid receptors and which have kappa inverse agonist, kappa biased agonist, kappa antagonist, kappa partial agonist, or kappa agonist activity are needed to provide improved methods for the treatment of affective disorders and other conditions for which kappa opioid receptor signaling plays a role in the pathogenesis of disease.

SUMMARY OF THE INVENTION

The invention is based on the discovery of compounds that are selective for kappa opioid receptors. The modulation of activity at kappa opioid receptors can be useful for the treatment of mood disorders. For example, the compounds exhibiting antagonist activity, biased agonist, or inverse agonist activity at kappa receptors are useful for the treatment of depressive disorders, among other conditions. The compounds exhibiting partial agonist or biased agonist activity at kappa receptors are useful for the treatment of bipolar disorder, e.g., as mood stabilizers, among other conditions. The compounds exhibiting full agonist or biased agonist activity at kappa receptors are useful for the treatment of the manic phase of bipolar disorder, among other conditions.

In a first aspect, the invention features a compound of formula I:

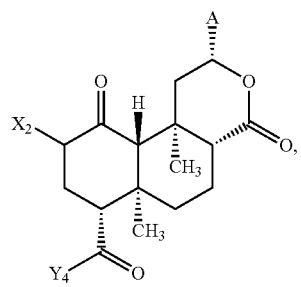

(I)

or a pharmaceutically acceptable salt thereof. In formula I, A is selected from $C(O)Y_{13}$, $C(O)X_{13}$, $CH(OR^A)X_{13}$, $CH_2Z_{13}$,

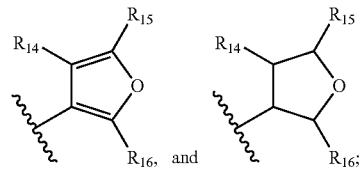

$X_2$ is selected from $OR_2$, O-acyl, $OC(O)Z_2$, $SR_2$, S-acyl, $SC(O)Z_2$, $NR_{21}R_{22}$, $NR_2$-acyl, and $NR_2C(O)Z_2$; $Z_2$ is $OR_2$, $SR_2$, or $NR_{21}R_{22}$; $Y_4$ is selected from $OR_4$, $SR_4$, and $NR_{23}R_{24}$; $X_{13}$ is selected from $C_{2-7}$ heterocyclyl, $C_{6-12}$ aryl, $C_{7-14}$ alkaryl, $C_{3-10}$ alkheterocyclyl, and $C_{1-8}$ heteroalkyl; $Y_{13}$ is selected from $OR_{13}$, $SR_{13}$, and $NR_{25}R_{26}$; $Z_{13}$ is selected from O—$R_{13}$, O—$X_{13}$, O-acyl, $OC(O)R_{13}$, S—$R_{13}$, S—$X_{13}$, S-acyl, $SC(O)R_{13}$, $NR_{25}R_{26}$, $NR_{13}$-acyl, NH—$X_{13}$, NHC(O)NH—$R_{13}$, and $NHC(O)OR_{13}$; each of $R_{14}$, $R_{15}$, and $R_{16}$ is, independently, selected from halide, $OR^B$, $C_{1-4}$ alkyl, $C_{2-4}$ alkenyl, $C_{2-4}$ alkynyl; and each of $R^A$, $R^B$, $R_2$, $R_4$, $R_{13}$, $R_{21}$, $R_{22}$, $R_{23}$, $R_{24}$, $R_{25}$, and $R_{26}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{21}$ and $R_{22}$, $R_{23}$ and $R_{24}$, and $R_{25}$ and $R_{26}$, combine to form a heterocyclic ring containing a nitrogen atom.

In certain embodiments, the compound is further described by formula IIa or IIb:

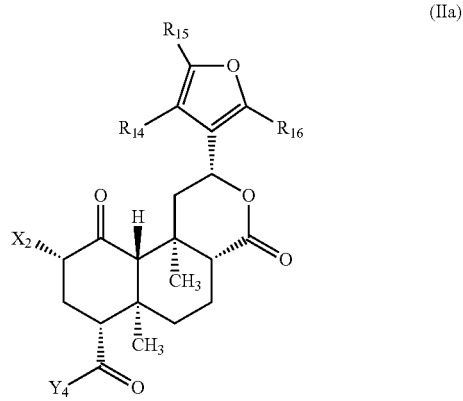

(IIa)

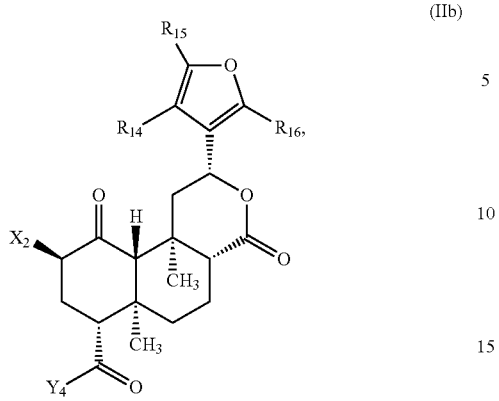

(IIb)

or a pharmaceutically acceptable salt thereof. In formula IIa and IIb, $X_2$, $Y_4$, $R_{14}$, $R_{15}$, and $R_{16}$ are as defined in formula I. In certain embodiments, of the compounds of formula IIa or IIb, $Y_4$ is $OCH_3$; $X_2$ is $OCH_2OCH_3$; $R_{14}$ and $R_{15}$ are H; and $R_{16}$ is fluorine or iodine (including radiolabelled compounds, such as $^{18}F$ or $^{125}I$ labeled compounds).

In other embodiments, the compound is further described by formula IIIa or IIIb:

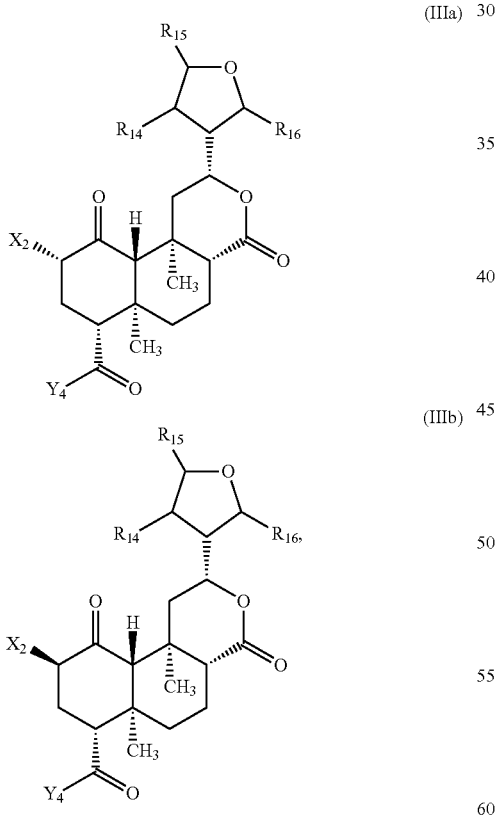

(IIIa)

(IIIb)

or a pharmaceutically acceptable salt thereof. In formula IIIa and IIIb, $X_2$, $Y_4$, $R_{14}$, $R_{15}$, and $R_{16}$ are as defined in formula I.

In still other embodiments, the compound is further described by formula IVa or IVb:

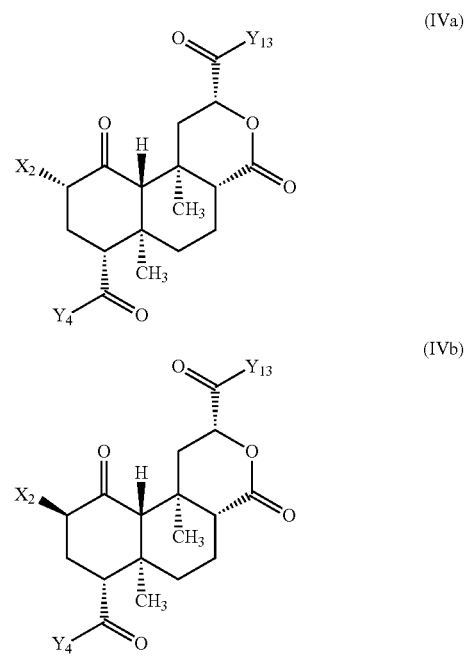

(IVa)

(IVb)

or a pharmaceutically acceptable salt thereof. In formula IVa and IVb, $X_2$, $Y_4$, and $Y_{13}$ are as defined in formula I.

In certain embodiments, the compound is further described by formula Va or Vb:

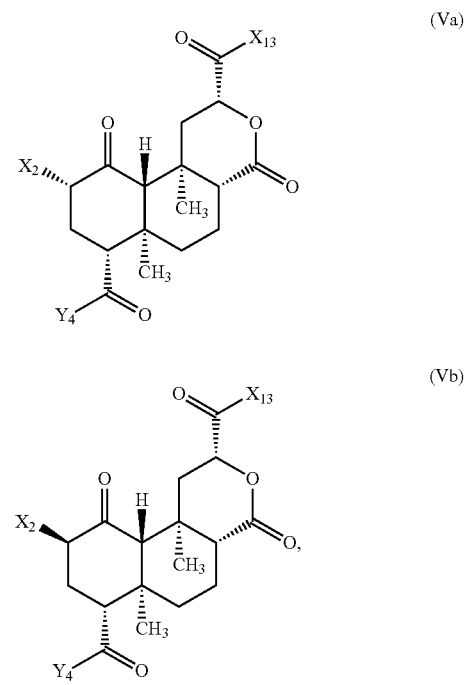

(Va)

(Vb)

or a pharmaceutically acceptable salt thereof. In formula Va and Vb, $X_2$, $Y_4$, and $X_{13}$ are as defined in formula I.

In other embodiments, the compound is further described by formula VIa or VIb:

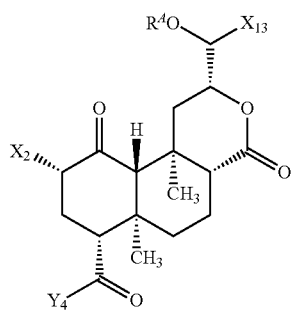

(VIa)

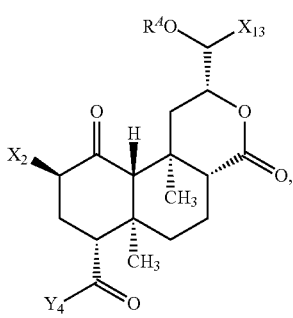

(VIb)

or a pharmaceutically acceptable salt thereof. In formula VIa and VIb, $X_2$, $Y_4$, $R^A$, and $X_{13}$ are as defined in formula I.

In still other embodiments, the compound is further described by formula VIIa or VIIb:

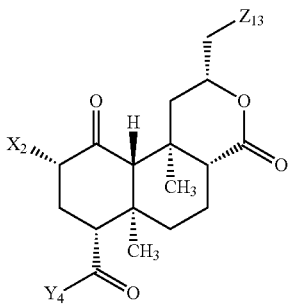

(VIIa)

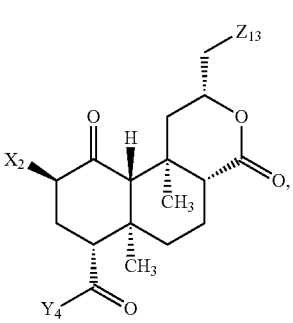

(VIIb)

or a pharmaceutically acceptable salt thereof. In formula VIIa and VIIb, $X_2$, $Y_4$, and $Z_{13}$ are as defined in formula I.

The invention further features a compound of formula VIII:

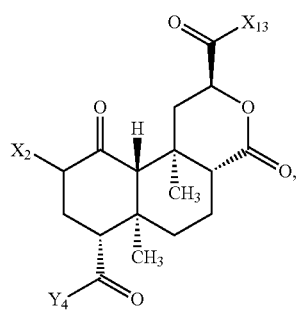

(VIII)

or a pharmaceutically acceptable salt thereof. In formula VIII, $X_2$ is selected from $OR_2$, O-acyl, $OC(O)Z_2$, $SR_2$, S-acyl, $SC(O)Z_2$, $NR_{21}R_{22}$, $NR_2$-acyl, and $NR_2C(O)Z_2$; $Z_2$ is $OR_2$, $SR_2$, or $NR_{21}R_{22}$; $Y_4$ is selected from $OR_4$, $SR_4$, and $NR_{23}R_{24}$; $X_{13}$ is selected from $C_{2-7}$ heterocyclyl, $C_{6-12}$ aryl, $C_{7-14}$ alkaryl, $C_{3-10}$ alkheterocyclyl, and $C_{1-8}$ heteroalkyl; and each of $R_2$, $R_4$, $R_{21}$, $R_{22}$, $R_{23}$, and $R_{24}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{21}$ and $R_{22}$, and $R_{23}$ and $R_{24}$ combine to form a heterocyclic ring containing a nitrogen atom.

The invention further features a compound of formula IX:

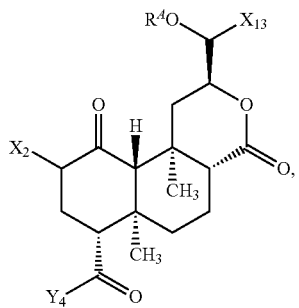

(IX)

or a pharmaceutically acceptable salt thereof. In formula IX, $X_2$ is selected from $OR_2$, O-acyl, $OC(O)Z_2$, $SR_2$, S-acyl, $SC(O)Z_2$, $NR_{21}R_{22}$, $NR_2$-acyl, and $NR_2C(O)Z_2$; $Z_2$ is $OR_2$, $SR_2$, or $NR_{21}R_{22}$; $Y_4$ is selected from $OR_4$, $SR_4$, and $NR_{23}R_{24}$; $X_{13}$ is selected from $C_{2-7}$ heterocyclyl, $C_{6-12}$ aryl, $C_{7-14}$ alkaryl, $C_{3-10}$ alkheterocyclyl, and $C_{1-8}$ heteroalkyl; and each of $R^A$, $R_2$, $R_4$, $R_{21}$, $R_{22}$, $R_{23}$, and $R_{24}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{21}$ and $R_{22}$, and $R_{23}$ and $R_{24}$ combine to form a heterocyclic ring containing a nitrogen atom.

The invention also features a compound of formula X:

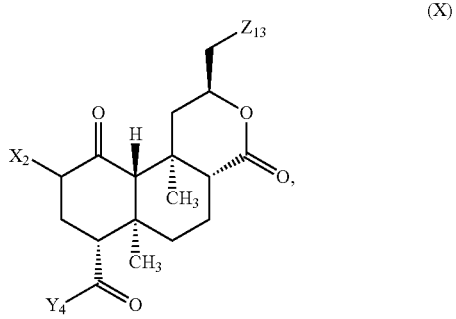

(X)

or a pharmaceutically acceptable salt thereof. In formula X, $X_2$ is selected from $OR_2$, O-acyl, $OC(O)Z_2$, $SR_2$, S-acyl, $SC(O)Z_2$, $NR_{21}R_{22}$, $NR_2$-acyl, and $NR_2C(O)Z_2$; $Z_2$ is $OR_2$, $SR_2$, or $NR_{21}R_{22}$; $Y_4$ is selected from $OR_4$, $SR_4$, and $NR_{23}R_{24}$; $X_{13}$ is selected from $C_{2-7}$ heterocyclyl, $C_{6-12}$ aryl, $C_{7-14}$ alkaryl, $C_{3-10}$ alkheterocyclyl, and $C_{1-8}$ heteroalkyl; $Z_{13}$ is selected from $O-R_{13}$, $O-X_{13}$, O-acyl, $OC(O)R_{13}$, $S-R_{13}$, $S-X_{13}$, S-acyl, $SC(O)R_{13}$, $NR_{25}R_{26}$, $NR_{43}$-acyl, $NH-X_{13}$, $NHC(O)NH-R_{13}$, and $NHC(O)OR_{13}$; and each of $R^A$, $R_2$, $R_4$, $R_{13}$, $R_{21}$, $R_{22}$, $R_{23}$, $R_{24}$, $R_{25}$, and $R_{26}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{21}$ and $R_{22}$, $R_{23}$ and $R_{24}$, and $R_{25}$ and $R_{26}$, combine to form a heterocyclic ring containing a nitrogen atom.

In a related aspect, the invention features a compound of formula XI:

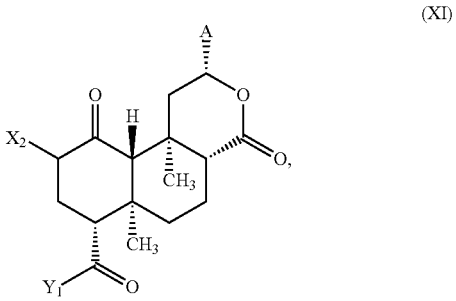

(XI)

or a pharmaceutically acceptable salt thereof. In formula XI, A is selected from

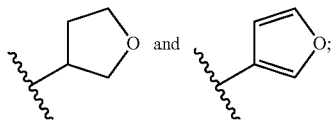 [SMILES: *C1CCOC1 ; *c1ccoc1]

and $X_2$ is selected from $O-R_2$, O-acyl, $OC(O)Z_2$, $S-R_2$, S-acyl, $SC(O)Z_2$, $NR_{16}R_{17}$, NH-acyl, $NHC(O)NH$-acyl, and $NHC(O)Z_2$; $Y_1$ is selected from $OR_{11}$, $SR_{11}$, and $NR_{12}R_{13}$; $Z_2$ is $OR_2$, $SR_2$, or $NR_{16}R_{17}$; and each of $R_2$, $R_{11}$, $R_{12}$, $R_{13}$, $R_{16}$, and $R_{17}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl or one or more of $R_{12}$ and $R_{13}$, and $R_{16}$ and $R_{17}$, combine to form a heterocyclic ring containing a nitrogen atom. In certain embodiments, $Y_1$ is $OCH_3$. In particular embodiments, the compound of formula XI is selected from 12-epi-salvinorin B propionate, 12-epi-salvinorin B butanoate, 12-epi-salvinorin B methylcarbamate, 12-epi-salvinorin B carbamate, 12-epi-salvinorin B methoxymethyl ether, 12-epi-salvinorin B n-butyl ether, 12-epi-salvinorin B allyl ether, 12-epi-salvinorin B ethyl ether, 12-epi-salvinorin B n-propyl ether, (2R,4aR,6aR,7R,9R,10aS,10bR)-methyl 9-amino-2-(furan-3-yl)-dodecahydro-6a,10b-dimethyl-4,10-dioxo-1H-benzo[f]iso-chromene-7-carboxylate, (2R,4aR,6aR,7R,9R,10aS,10bR)-methyl 9-(ethylamino)-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 2-(furan-3-yl)-dodecahydro-9-(isopropylamino)-6a,10b-dimethyl-4,10-dioxo-1H-benzo[f]isochromene-7-carboxylate, (2R,4aR,6aR,7R,9S,10aS,10bR)-methyl 9-amino-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 9-(N-methylacetamido)-2-(furan-3-yl)-dodecahydro-6a,10b-dimethyl-4,10-dioxo-1H-benzo[f]isochromene-7-carboxylate, (2R,4aR,6aR,7R,9S,10aS,10bR)-methyl 9-(ethylamino)-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 9-(N-methylpropionamido)-2-(furan-3-yl)-dodecahydro-6a,10b-dimethyl-4,10-dioxo-1H-benzo[f]isochromene-7-carboxylate, 2-epi-12-epi-salvinorin A, 2-epi-12-epi-salvinorin B, 2-epi-12-epi-salvinorin B propionate, 2-epi-12-epi-salvinorin B butanoate, 2-epi-12-epi-salvinorin B methoxymethyl ether, 2-epi-12-epi-salvinorin B ethyl ether, 2-epi-12-epi-salvinorin B propyl ether, (2R,4aR,6aR,7R,9S,10aS,10bR)-methyl 9-(N-methylpropionamido)-2-(furan-3-yl)-dodecahydro-6a,10b-dimethyl-4,10-dioxo-1H-benzo[f]isochromene-7-carboxylate, 12-epi-16-bromosalvinorin A, 12-epi-16-vinylsalvinorin A, (2R,4aR,6aR,7R,9S,10aS,10bR)-methyl 9-acetoxy-2-((R)-(furan-2-yl)(hydroxy)methyl)-dodecahydro-6a,10b-dimethyl-4,10-dioxo-1H-benzo[f]isochromene-7-carboxylate, 12-epi-13-ketopyrazinylsalvinorin, 12-epi-13-ketothiofuranylsalvinorin, 12-epi-13-ketofuranylsalvinorin, and (2R,4aR,6aR,7R,9S,10aS,10bR)-methyl 9-acetoxy-dodecahydro-2-((S)-tetrahydrofuran-3-yl)-6a,10b-dimethyl-4,10-dioxo-1H-benzo[f]isochromene-7-carboxylate, and pharmaceutically acceptable salts thereof.

The following chemical names may be used interchangeably herein.

| Chemical Name | Equivalent Chemical Name |
| --- | --- |
| 12-epi-salvinorin B propionate = | 2-propionyl-12-epi-salvinorin B |
| 12-epi-salvinorin B butanoate = | 2-butyryl-12-epi-salvinorin B |
| 12-epi-salvinorin B = methylcarbamate | 2-(O-(N-methyl)formamide)-12-epi-salvinorin B |
| 12-epi-salvinorin B carbamate = | 2-(O-formamide)-12-epi-salvinorin B |
| 12-epi-salvinorin B methoxymethyl ether = | 2-methoxymethy-12-epi-salvinorin B |
| 12-epi-salvinorin B n-butyl ether = | 2-n-butoxy-12-epi-salvinorin B |
| 12-epi-salvinorin B allyl ether = | 2-allyloxy-12-epi-salvinorin B |
| 12-epi-salvinorin B ethyl ether = | 2-ethoxy-12-epi-salvinorin B |
| 12-epi-salvinorin B n-propyl ether = | 2-propoxy-12-epi-salvinorin B |
| (2R,4aR,6aR,7R,9R,10aS,10bR)-methyl 9-amino-2-(furan-3-yl)-dodecahydro-6a,10b-dimethyl-4,10-dioxo-1H-benzo[f]isochromene-7-carboxylate | 2-epi-amino-12-epi-salvinorin |

-continued

| Chemical Name | Equivalent Chemical Name |
|---|---|
| (2R,4aR,6aR,7R,9R,10aS,10bR)- = methyl 9-(ethylamino)-2-(furan-3-yl)-dodecahydro-6a,10b-dimethyl-4,10-dioxo-1H-benzo[f]isochromene-7-carboxylate | 2-epi-(N-ethylamino)-12-epi-salvinorin |
| (2R,4aR,6aR,7R,9R,10aS,10bR)- = methyl 2-(furan-3-yl)-dodecahydro-9-(isopropylamino)-6a,10b-dimethyl-4,10-dioxo-1H-benzo[f]isochromene-7-carboxylate | 2-epi-N-isopropyl-12-epi-salvinorin |
| (2R,4aR,6aR,7R,9S,10aS,10bR)- = methyl 9-amino-2-(furan-3-yl)-dodecahydro-6a,10b-dimethyl-4,10-dioxo-1H-benzo[f]isochromene-7-carboxylate | 2-amino-12-epi-salvinorin |
| (2R,4aR,6aR,7R,9R,10aS,10bR)- = methyl 9-(N-methylacetamido)-2-(furan-3-yl)-dodecahydro-6a,10b-dimethyl-4,10-dioxo-1H-benzo[f]isochromene-7-carboxylate | 2-epi-(N-methylacetamide)-12-epi-salvinorin |
| (2R,4aR,6aR,7R,9S,10aS,10bR)- = methyl 9-(ethylamino)-2-(furan-3-yl)-dodecahydro-6a,10b-dimethyl-4,10-dioxo-1H-benzo[f]isochromene-7-carboxylate | 2-(N-ethylamino)-12-epi-salvinorin |
| (2R,4aR,6aR,7R,9R,10aS,10bR)- = methyl 9-(N-methylpropionamido)-2-(furan-3-yl)-dodecahydro-6a,10b-dimethyl-4,10-dioxo-1H-benzo[f]isochromene-7-carboxylate | 2-epi-(N-methylpropionamide)-12-epi-salvinorin |
| 2-epi-12-epi-salvinorin A = | 2-epi-12-epi-salvinorin A |
| 2-epi-12-epi-salvinorin B = | 2-epi-12-epi-salvinorin B |
| 2-epi-12-epi-salvinorin B propionate = | 2-epi-2-propionyl-12-epi-salvinorin B |
| 2-epi-12-epi-salvinorin B butanoate = | 2-epi-butyryl-12-epi-salvinorin B |
| 2-epi-12-epi-salvinorin B methoxymethyl ether = | 2-epi-methoxymethy-12-epi-salvinorin B |
| 2-epi-12-epi-salvinorin B ethyl ether = | 2-epi-ethoxy-12-epi-salvinorin B |
| 2-epi-12-epi-salvinorin B propyl ether = | 2-epi-propoxy-12-epi-salvinorin B |
| (2R,4aR,6aR,7R,9S,10aS,10bR)- = methyl 9-(N-methylpropionamido)-2-(furan-3-yl)-dodecahydro-6a,10b-dimethyl-4,10-dioxo-1H-benzo[f]isochromene-7-carboxylate | 2-(N-methylpropionamide)-12-epi-salvinorin |
| 12-epi-16-bromosalvinorin A = | 12-epi-16-bromosalvinorin A |
| 12-epi-16-vinylsalvinorin A = | 12-epi-16-vinylsalvinorin A |
| (2R,4aR,6aR,7R,9S,10aS,10bR)- = methyl 9-acetoxy-24(R)-(furan-2-yl)(hydroxy)methyl)-dodecahydro-6a,10b-dimethyl-4,10-dioxo-1H-benzo[f]isochromene-7-carboxylate | 12-epi-13-hydroxyfuranylsalvinorin |
| 12-epi-13-ketopyrazinylsalvinorin = | 12-epi-13-ketopyrazinylsalvinorin |
| 12-epi-13-ketothiofuranylsalvinorin = | 12-epi-13-ketothiofuranylsalvinorin |
| 12-epi-13-ketofuranylsalvinorin = | 12-epi-13-ketofuranylsalvinorin |
| (2R,4aR,6aR,7R,9S,10aS,10bR)- = methyl 9-acetoxy-dodecahydro-2-((S)-tetrahydrofuran-3-yl)-6a,10b-dimethyl-4,10-dioxo-1H-benzo[f]isochromene-7-carboxylate | 12-epi-13-tetrahydrofuranylsalvinorin |

In a related aspect, the invention features a compound of formula XII:

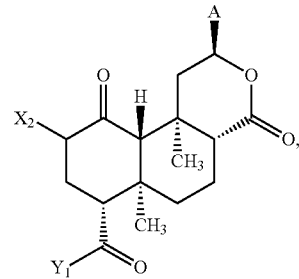

(XII)

or a pharmaceutically acceptable salt thereof. In formula XII, A is

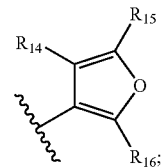

$X_2$ is selected from O—$R_2$, O-acyl, OC(O)$Z_2$, S—$R_2$, S-acyl, SC(O)$Z_2$, $NR_6R_7$, NH-acyl, NHC(O)NH-acyl, and NHC(O)$Z_2$; $Y_1$ is selected from $OR_{11}$, $SR_{11}$, and $NR_{12}R_{13}$; $Z_2$ is $OR_2$, $SR_2$, or $NR_6R_7$; each of $R_2$, $R_{11}$, $R_{12}$, $R_{13}$, $R_6$, and $R_7$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl or one or more of $R_{12}$ and $R_{13}$, and $R_6$ and $R_7$, combine to form a heterocyclic ring containing a nitrogen atom; and each of $R_{14}$, $R_{15}$, and $R_{16}$ is selected from H, Br, and CH=$CH_2$ provided at least one of $R_{14}$, $R_{15}$, and $R_{16}$ is not H. In certain embodiments, $Y_1$ is $OCH_3$.

In one particular embodiment of any of the compounds of formulas I-XII, the compound is not 12-epi-salvinorin A.

Any of the compounds described herein can be a selective, kappa inverse agonist selective kappa antagonist, a selective kappa receptor partial agonist, or a selective kappa agonist.

The invention features a method for treating a mood disorder in a mammal, e.g., a human patient, by administering an effective amount of a selective kappa receptor antagonist, biased agonist, or inverse agonist of the invention. These compounds are particularly useful for treating depressive disorders and disorders associated with depression, such as major depression, dysthymia, bipolar disorder (manic depression), drug withdrawal, and post traumatic stress disorder; however, any psychologic or psychiatric disorder having symptoms that include abnormalities of mood, such as schizoaffective disorder, schizophrenia, anxiety disorder, panic disorder, post traumatic stress disorder, phobic disorder, borderline personality disorder, schizoid disorder, or schizotypal disorder, are amenable to treatment according to the present methods.

The invention features a method for treating bipolar disorder in a mammal, e.g., a human patient, in need thereof, by administering an effective amount of a selective kappa receptor partial agonist or selective kappa receptor biased agonist of the invention.

The invention further features a method for stabilizing the mood of a mammal, e.g., a human patient, diagnosed with a mood disorder by administering an effective amount of a selective kappa receptor partial agonist or biased agonist of the invention.

The invention features a method for treating mania in a mammal, e.g., a human patient, in need thereof, by administering an effective amount of a selective kappa receptor agonist or biased agonist of the invention. Selective kappa receptor agonists are particularly useful for treating mania associated with bipolar disorder, acute mania, and chronic mania. The mania can occur in a single episode or be recurring.

The selective kappa receptor antagonists, partial agonists, inverse agonists, biased agonists, and agonists can be administered systemically, including, for example, by intravenous, intramuscular, or subcutaneous injection, orally, or by topical or transdermal application, provided that the kappa receptor antagonist is capable of penetrating the blood-brain barrier sufficiently to be effective. Alternatively, the kappa-selective compounds can be centrally administered using, for example, by an intrathecal, intracerebroventricular, or intraparenchemal injection.

As used herein "substantially pure" refers to a composition containing a compound described herein which possesses the unnatural epimer configuration at C12 and which contains less than 10%, 5%, 2%, 1%, 0.05%, or 0.01% (w/w) of the corresponding naturally occurring configuration at C12 (e.g., greater than 90% 12-episalvinorin A and less than 10% salvinorin A). The amount of each C12 isomer present in the mixture can be determined using chromatographic methods. Any compound of the invention having the 12-epi configuration can optionally be substantially pure.

By "selective kappa antagonist" is meant any chemical compound which has affinity for the kappa opioid receptor, substantially no agonist activity, and produces less than 15% of the maximal response in comparison to dynorphin A. The selective kappa antagonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

By "selective kappa receptor partial agonist" is meant any chemical compound which has affinity for the kappa opioid receptor and agonist activity, but produces only a partial (i.e., submaximal) response of between 15% and 85% in comparison to dynorphin A, an endogenous neurotransmitter of the kappa opioid receptor. The selective kappa partial agonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

By "selective kappa receptor agonist" is meant any chemical compound which has affinity for the kappa opioid receptor and agonist activity, and produces at least 85% of the maximal response in comparison to dynorphin A, an endogenous neurotransmitter of the kappa opioid receptor. The selective kappa agonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

By "selective kappa receptor inverse agonist" is meant any chemical compound which has affinity for the kappa opioid receptor and exerts the opposite pharmacological effect of dynorphin A.

By "selective kappa receptor biased agonist" is meant any chemical compound which has affinity for the kappa opioid receptor and stabilizes a subset of the possible active conformations of the receptor, generating only part of the full response profile relative to the unliganded state. Embodied in the concept of multiple active states that reflect different receptor conformations, a selective kappa receptor biased agonist will exhibit different agonist, antagonist or inverse agonist properties, depending on the signaling output being measured.

The term "administration" or "administering" refers to a method of giving a dosage of a pharmaceutical composition to a patient, where the method is, e.g., topical, transdermal, oral, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

By "depressive disorder" is meant any psychologic or psychiatric disorder which is associated with symptoms of depression. Treatable depressive disorders can be characterized by an inhibition or reduction of dopaminergic function in the nucleus accumbens, e.g., major depression, dysthymia, bipolar disorder (manic depression), drug withdrawal, and post-traumatic stress disorder.

By "effective amount" is meant is meant an amount of a compound of the invention which has a therapeutic effect, e.g., which prevents, reduces, or eliminates the depression, mania, mood fluctuations, or reduces CREB activation. This amount, an effective amount, can be routinely determined by one of skill in the art, by animal testing and/or clinical testing, and will vary, depending on several factors, such as the particular disorder to be treated and the particular compound of the invention used. This amount can further depend upon the subject's weight, sex, age and medical history.

In the generic descriptions of compounds of this invention, the number of atoms of a particular type in a substituent group is generally given as a range, e.g., an alkyl group containing from 1 to 7 carbon atoms or $C_{1-8}$ alkyl. Reference to such a range is intended to include specific references to groups having each of the integer number of atoms within the specified range. For example, an alkyl group from 1 to 8 carbon atoms includes each of $C_1$, $C_2$, $C_3$, $C_4$, $C_5$, $C_6$, $C_7$, and $C_8$. A $C_{1-8}$ heteroalkyl, for example, includes from 1 to 7 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-8}$ alkyl group may be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{1-8}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-8}$ alkenyl" is meant a branched or unbranched hydrocarbon group containing one or more double bonds and having from 2 to 8 carbon atoms. A $C_{2-8}$ alkenyl may optionally include monocyclic or polycyclic rings, in which each ring desirably has from three to six members. The $C_{2-8}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{2-8}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-8}$ alkynyl" is meant a branched or unbranched hydrocarbon group containing one or more triple bonds and having from 2 to 8 carbon atoms. A $C_{2-8}$ alkynyl may optionally include monocyclic, bicyclic, or tricyclic rings, in which each ring desirably has five or six members. The $C_{2-8}$ alkynyl group may be substituted or unsubstituted. Exemplary substituents include alkoxy, aryloxy, sulfhydryl, alkylthio, arylthio, halide, hydroxy, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{2-8}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butyryl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-7}$ heterocyclyl" is meant a stable 5- to 7-membered monocyclic or 7- to 14-membered bicyclic heterocyclic ring which is saturated partially unsaturated or unsaturated (aromatic), and which consists of 2 to 7 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulthydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-8}$ heteroalkyl" is meant a branched or unbranched alkyl, alkenyl, or alkynyl group having from 1 to 8 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, cyano, nitrilo, NH-acyl, amino, aminoalkyl, disubstituted amino, quaternary amino, hydroxyalkyl, hydroxyalkyl, carboxyalkyl, and carboxyl groups. Examples of $C_{1-8}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "hydroxyalkyl" is meant a chemical moiety with the formula —(R)—OH, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "alkoxy" is meant a chemical substituent of the formula —OR, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R")(R''')$^+$, wherein R, R', R", and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "acyl" is meant a chemical moiety with the formula R-C(O)—, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, $C_{1-8}$ heteroalkyl (including amino acid acyls), or the acyl is a fatty acid acyl.

By "amino acid acyl" is meant a chemical moiety with the formula R—C(O)—, wherein R—C(O)— is selected from natural and unnatural amino acids.

By "fatty acid acyl" is meant a chemical moiety with the formula R—C(O)—, wherein R is a partially-saturated straight chain or branched hydrocarbon group having from 14 to 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexanoyl.

Because the compounds of the invention are highly selective for the kappa opioid receptor, they can be used in the methods of the invention to treat conditions for which kappa opioid receptor signaling plays a role in the pathogenesis of disease without directly influencing signaling at other receptors and producing unwanted side-effects.

Other features and advantages of the invention will be apparent from the following Detailed Description, the drawings, and the claims.

DETAILED DESCRIPTION

Figure 1:
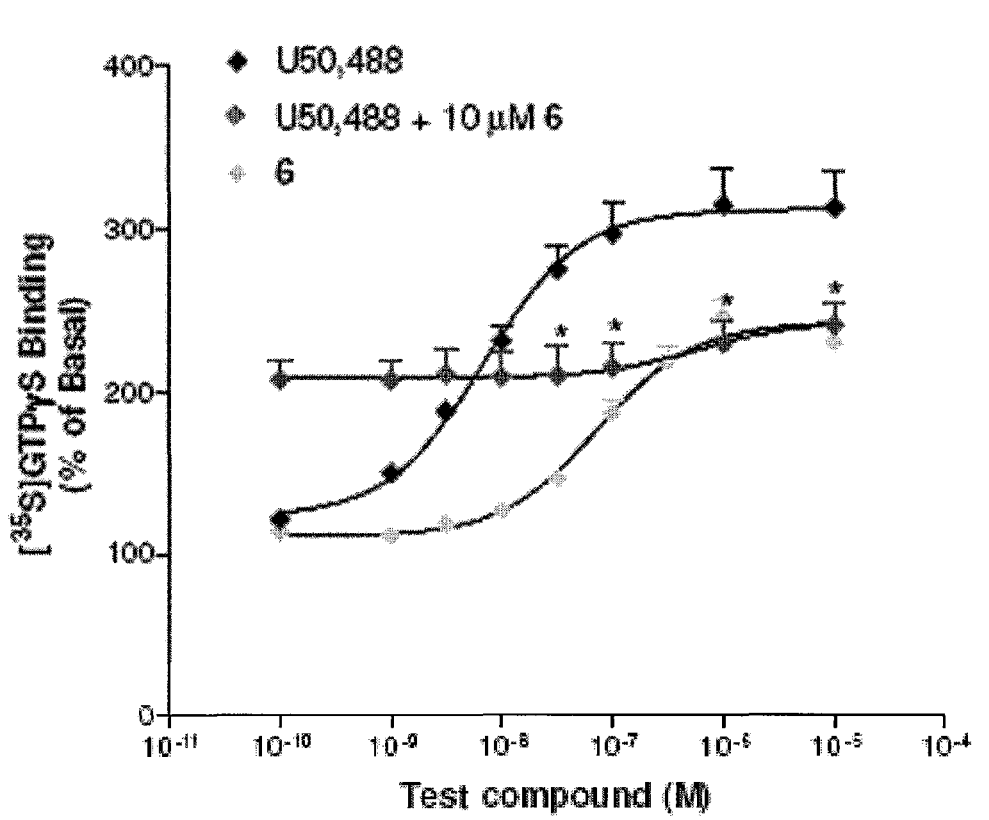
FIG. 1 is a graph showing the dose-response curves of compound 6 (12-epi-Salvinorin A) and U50,488 in the [$^{35}$S] GTPγS functional assay. Compound 6 exhibits partial agonist properties in the [$^{35}$S]GTPγS assay. At 10 μM, compound 6 significantly reduced [$^{35}$S]GTPγS binding induced by U50, 488 ranging from $3\times10^{-8}$ to $10^{-5}$ M (Student's t test, *, P<0.01).
Figure 2:
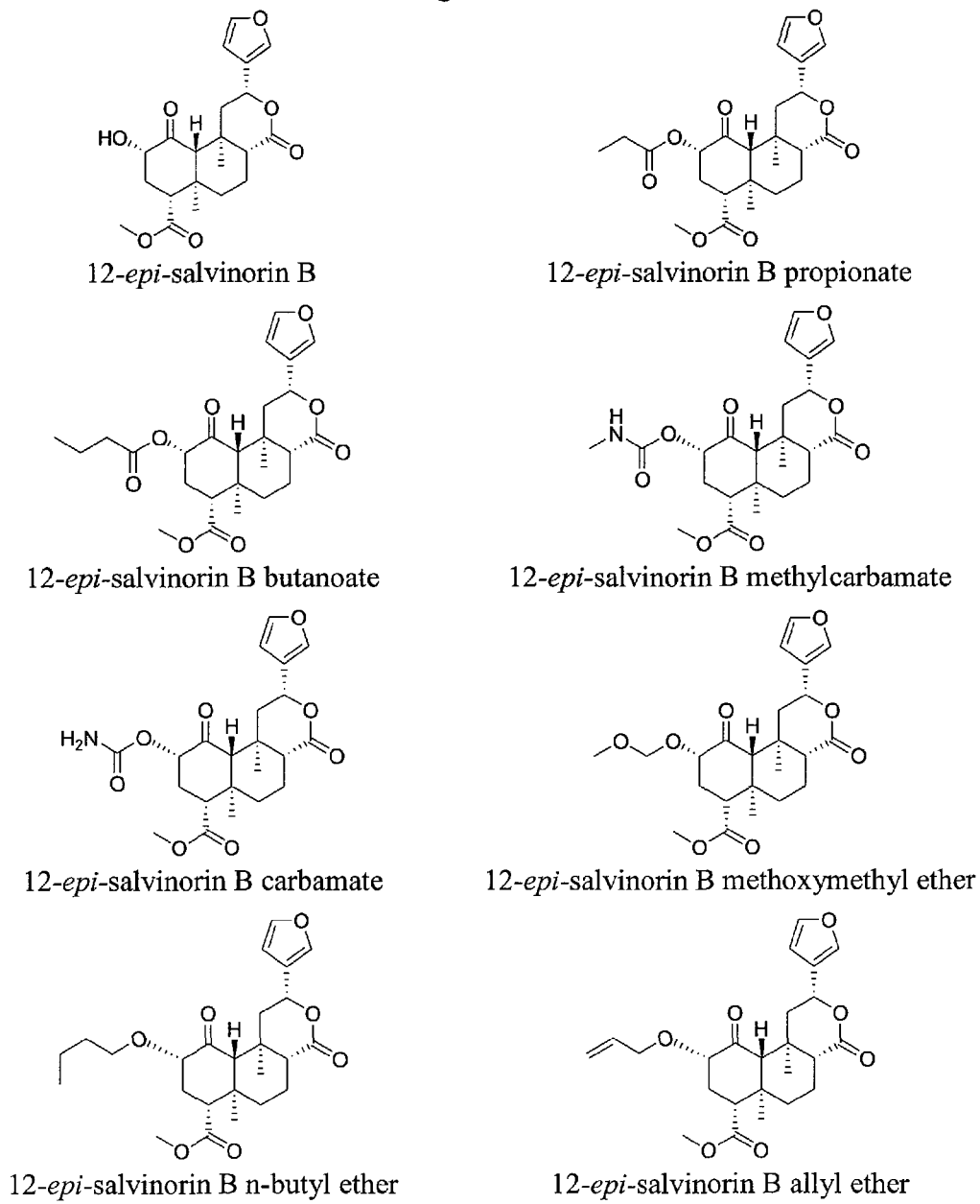
FIG. 2 is a drawing depicting compounds of the invention.

We have made compounds that are useful for the treatment of depression and/or mania. The compounds are described by formulas I-XII. These compounds can be prepared as described in the Examples.

Assays

To determine their affinity for specific opioid receptors, the compounds described herein can be characterized in radioligand receptor binding assays, using ligands that are specific for the mu, delta and kappa receptors. For example, the binding assays may utilize guinea pig brain membranes or stably transfected Chinese Hamster Ovary (CHO) cells expressing each of the three opioid receptors, as described in Example 8.

To determine their efficacy (e.g., agonist, partial agonist, antagonist) at a specific opioid receptor, compounds can be characterized by [$^{35}$S]GTPγS binding assay, as described in Example 8.

A symptom of clinical depression that can be modeled in rats is despair, a feeling of hopelessness. Symptoms of despair can be induced in rats using the forced swim test (FST), as described in Example 12, a highly validated model used to study antidepressant treatments.

Mania-like symptoms can be induced in rodents by the administration of psychomotor stimulant drugs such as cocaine or amphetamine. Psychostimulants produce a range of behaviors in animals that appear similar to mania, including hyperactivity, heightened sensory awareness and alertness, and changes in sleep patterns. Psychostimulant-induced hyperactivity is mediated by increased dopaminergic transmission in striatal regions. Based on this information, psychostimulant-induced hyperactivity in rodents has become a standard model for the screening of antimanic drugs. The mania-like effects of these psychomotor stimulants can be studied in behavioral assays that quantify locomotor activity ("open field activity") or the function of brain reward systems ("place conditioning" or "intracranial self-stimulation (ICSS)) (see Example 13). The Antimanic-like effects of salvinorin derivatives can be identified by the ability of these agents to reduce, attenuate, or block the stimulant or rewarding effects of cocaine or amphetamine in these assays. For further details see, for example, Einat and Belmaker Animal models of bipolar disorder: From a single episode to progressive cycling models; In: "Contemporary Issues in Modeling Psychopathology" Myslobodsky M, Weiner I (Eds.), 2000; London: Kluver Academic, New York, pp 165-179.

Therapy

The compounds described herein can be used for the treatment of mania, depressive disorders. Compounds of the invention can be particularly useful for treating major depression, dysthymia, bipolar disorder (manic depression), and post traumatic stress disorder; however, any psychologic or psychiatric disorder having symptoms that include abnormalities of mood or emotion are amenable to treatment according to the present methods. For example, the compounds can be used to treat disorders of mood, including, without limitation, Depression, Bipolar Disorder, Schizoaffective Disorder, Schizophrenia and other psychotic disorders, Anxiety Disorders, Panic Disorder, Traumatic Stress Disorders, Phobic Disorders, and Personality Disorders with abnormal mood, such as Borderline Personality Disorder, Schizoid and Schizotypal Disorders. For example, compounds having antagonist activity, biased agonist, or inverse agonist activity at kappa opioid receptors are useful for the treatment of depression; compounds having partial agonist or biased agonist activity at kappa opioid receptors are useful as mood stabilizers for the treatment of, for example, bipolar disorder; and compounds having agonist or biased agonist activity at kappa opioid receptors are useful for the treatment of mania.

The invention features a method of treating depressive disorders or mania by administering a compound having any of formulas I-XII. The compounds of the invention may be administered with a pharmaceutically acceptable diluent, carrier, or excipient, in unit dosage form. Administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of formulas I-XII can include isomers such as diastereomers and enantiomers, mixtures of isomers, including racemic mixtures, salts, solvates, and polymorphs thereof.

The formulations can be administered to patients in therapeutically effective amounts. For example, an amount is administered which prevents, reduces, or eliminates the depression, mania, mood fluctuations, or reduces CREB activation, respectively. Typical dose ranges are from about 0.001 µg/kg to about 2 mg/kg of body weight per day. Desirably, a dose of between 0.001 µg/kg and 1 mg/kg of body weight, or 0.005 µg/kg and 0.5 mg/kg of body weight, is administered.

The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Where the specification refers to a position of the salvinorin ring system, the position is identified according to the numbering system provided below.

numbering scheme

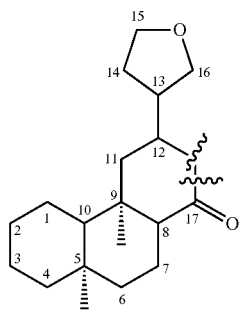

The synthesis of compounds of the invention may require selective protection and deprotection of alcohols, amines, and carboxylic acid functional groups in the salvinorin starting material. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, and carboxylic acid functionalities and the conditions required for their removal are provided in detail in "T. W. Green and P. G. M. Wuts: Protective Groups in Organic Synthesis" (2nd ed., 1991, John Wiley & Sons) and "P. J. Kocienski: Protecting Groups" (1994 Georg Thieme Verlag); each of which is incorporated herein by reference.

General methods. Reactions were carried out in flame-dried glassware under an argon atmosphere unless noted otherwise. Commercial reagents and solvents were used without further purification. Reactions were monitored by thin-layer chromatography (TLC) using either an ethanolic solution of vanillin and $H_2SO_4$ or an aqueous solution of ammonium molybdate, cerium sulfate, and $H_2SO_4$, and heat as developing agents. Products were purified using automated flash chromatography (50 µm silica gel), manual flash chromatography (230-400 mesh silica gel), or a Waters HPLC system (ELSD detector, Novapak column [6 µm silica, 7.8×300 mm]). $^1$H NMR and $^{13}$C NMR chemical shifts are referenced to residual solvent peaks as internal standards: $CDCl_3$ (7.26 and 77 ppm) or $CD_3OD$ (3.30 and 49 ppm).

Example 1

Synthesis of 12-epi-salvinorin A (6)

Compound 6 was prepared as described in Scheme 1.

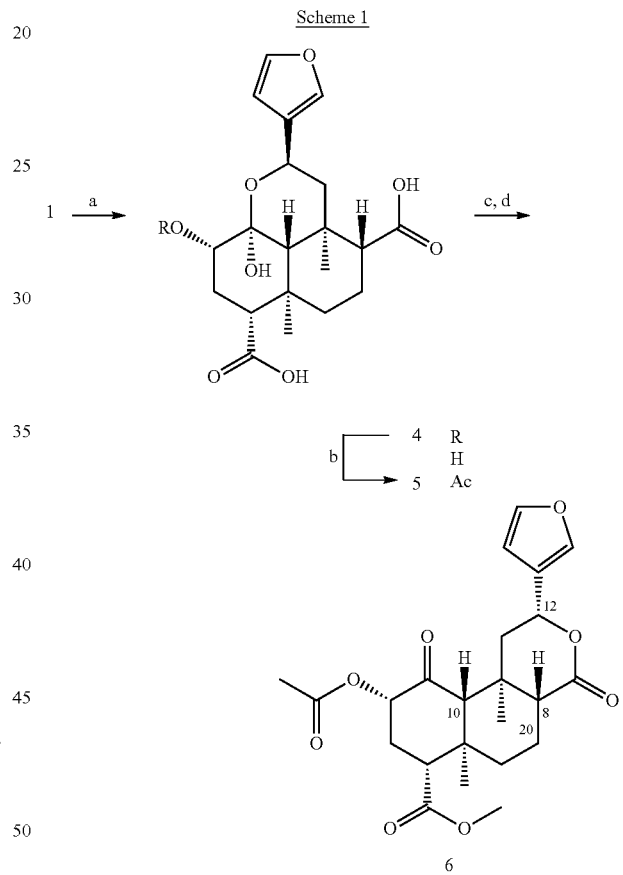

Scheme 1. Synthesis of 12-epi-salvinorin A. Reagents and conditions: (a) 5% aqueous KOH, 80° C., 95%; (b) $Ac_2O$, pyridine, r.t., 48%; (c) AcOH, 118° C.; (d) $TMSCHN_2$, $CH_3CN$, r.t., 19%, over two steps.

A solution of salvinorin A (1) (750 mg, 1.7 mmol) in aq KOH (5%, 50 mL) was refluxed for 2 h. The solution was cooled to room temperature and acidified to pH ~2 with aq HCl (5 M). The cloudy mixture was then extracted into EtOAc. Drying ($MgSO_4$) and concentration in vacuo gave 4 (650 mg, 95%) as a yellow foam. $R_f$ 0.21 (9:1, $CH_2Cl_2$/$CH_3OH$); $^1$H NMR (300 MHz, $CD_3OD$): δ 7.47 (dt, J=1.6, 0.8 Hz, 1H), 7.40 (t, J=1.7 Hz, 1H), 6.44 (dd, J=1.8, 0.7 Hz, 1H), 5.09 (dd, J=11.8, 1.6 Hz, 1H), 3.53 (dd, J=11.9, 5.0 Hz, 1H), 2.23 (dd, J=13.2, 2.7 Hz, 1H), 2.15 (dd, J=12.9, 3.0 Hz, 1H), 2.02-1.89 (m, 3H), 1.82 (dt, J=13.3, 3.1 Hz, 1H), 1.74-1.55 (m, 3H), 1.53 (s, 3H), 1.43-1.30 (m, 1H), 1.34 (s, 1H), 1.23 (s, 3H); $^{13}$C NMR (75 MHz, CD$_3$OD): δ 177.3, 176.6, 144.0, 140.6, 128.9, 110.1, 98.3, 75.2, 62.6, 56.8, 55.3, 55.3, 51.2, 41.4, 37.8, 37.1, 30.4, 22.4, 18.9, 16.1.

A solution of 4 (309 mg, 784 μmol) and Ac2O (90 μL, 942 μmol, 1.2 equiv) in pyridine (6 mL) was stirred at room temperature (42 h). The reaction was concentrated in vacuo and the residue purified by column chromatography (silica gel; 0-10% MeOH/CH$_2$Cl$_2$) to yield 5 (170 mg, 48%) as a white powder: R$_f$ 0.32 (9:1, CH$_2$Cl$_2$/CH$_3$OH); $^1$H NMR (300 MHz, CD$_3$OD): δ 7.38 (t, J=1.7 Hz, 1H), 7.32 (dd, J=0.8, 1.5 Hz, 1H), 6.35 (dd, J=0.7, 1.8 Hz, 1H), 5.06 (d, J=10.8 Hz, 1H), 4.80 (dd, J=4.8, 12.1 Hz, 1H), 2.31 (dd, J=2.7, 13.2 Hz, 1H), 2.20-1.99 (m, 6H), 1.94 (dd, J=2.0, 13.3 Hz, 1H), 1.90-1.82 (m, 1H), 1.73 (ddd, J=2.7, 4.6, 12.8 Hz, 1H), 1.67-1.57 (m, 2H), 1.55 (s, 3H), 1.47-1.30 (m, 2H), 1.25 (s, 3H); $^{13}$C NMR (75 MHz, CD$_3$OD): δ 177.2, 176.2, 172.2, 144.0, 140.1, 129.1, 109.8, 97.7, 77.4, 63.0, 56.7, 55.6, 55.2, 51.4, 41.4, 37.9, 37.1, 28.3, 22.4, 21.1, 18.8, 16.2.

A solution of 5 (102 mg, 234 μmol) in AcOH (2.3 mL) was refluxed (18 h). The reaction was concentrated in vacuo and the residue was diluted with i-PrOH and concentrated to remove excess AcOH. The residue was then dissolved in MeCN (2 mL) and TMSCHN2 (2.0 M in hexane, 6 equiv, 700 μL, 1.4 mmol) added. The solution was stirred at room temperature (25 min), concentrated in vacuo, and the residue purified by column chromatography (silica gel; 0-50% EtOAc/hexanes). Slow evaporation from EtOAc/hexanes yielded 6 (11 mg, 11%) as colorless needles, mp. 212-217° C. (dec); R$_f$ 0.27 (1:1, hexanes/EtOAc); $^1$H NMR (300 MHz, CDCl$_3$): δ 7.45-7.41 (m, 1H), 7.39 (t, J=1.7 Hz, 1H), 6.41 (dd, J=0.7, 1.8 Hz, 1H), 5.30 (dd, J=6.1, 11.6 Hz, 1H), 5.22-5.11 (m, 1H), 3.73 (s, 3H), 2.78 (dd, J=7.6, 9.2 Hz, 1H), 2.49-2.36 (m, 2H), 2.36-2.30 (m, 2H), 2.28 (dd, J=4.7, 7.0 Hz, 1H), 2.17 (s, 3H), 2.07-1.72 (m, 4H), 1.64 (dd, J=4.9, 14.0 Hz, 1H), 1.38 (s, 3H), 1.07 (s, 3H); $^{13}$C NMR (75 MHz, CDCl$_3$): δ 201.8, 173.1, 171.5, 170.0, 143.7, 139.8, 123.8, 108.7, 75.0, 70.3, 65.8, 53.4, 52.0, 47.3, 44.7, 42.3, 37.7, 35.2, 30.6, 21.2, 20.6, 18.2, 16.1; HRMS-ESI (m/z): [M+H]$^+$ calcd for C$_{23}$H$_{28}$O$_8$, 433.1862; found, 433.1847.

In addition to being of interest as a therapeutic agent, 12-epi-salvinorin A can be a useful starting material in the synthesis of salvinorin derivatives having the unnatural stereochemistry at the 12 position of the salvinorin ring system.

Example 2

Syntheses of C-13 Alcohol and Ethers (Compounds 7-11)

C-13 alcohol and ethers were prepared as described in Scheme 2.

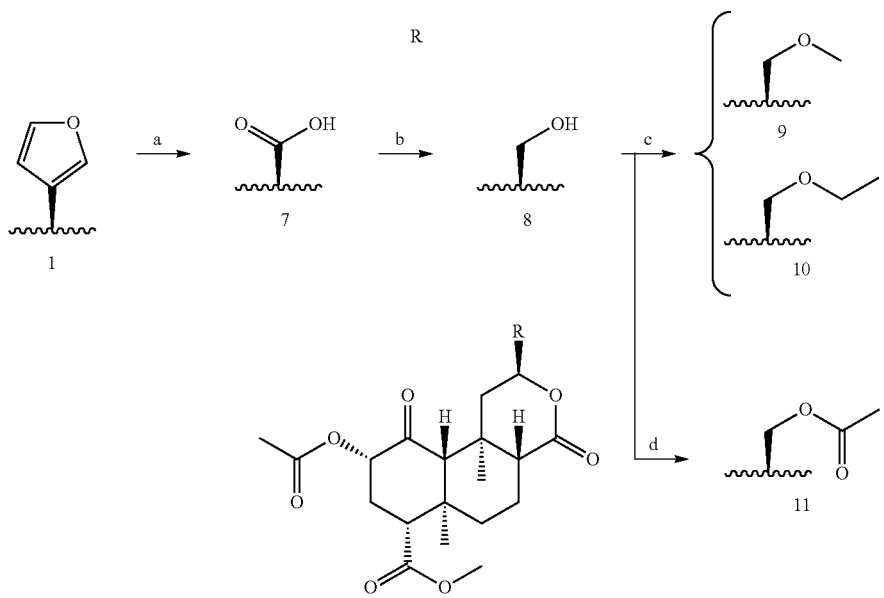

Scheme 2. Syntheses of C-13 alcohol and ethers. Reagents and conditions:
(a) NaIO$_4$, RuCl$_3$•3H$_2$O, CH$_2$Cl$_2$/CH$_3$CN/H$_2$O, 63%; (b) BH$_3$•THF, THF, 55° C., 46%; (c) RI, Ag$_2$O, CH$_3$CN, 60° C., 12-15%; (d) Ac$_2$O, Et$_3$N, CH$_2$Cl$_2$, r.t., 79%.

Salvinorin A was used to prepare compound 7 using the synthetic methodology described in Harding et al., *J. Nat. Prod.* 69:107 (2006).

Synthesis of Compound 8

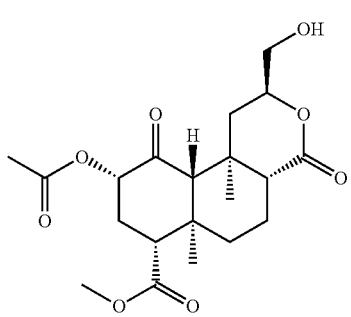

(8)

To a THF (3 mL) solution of 7 (157 mg, 382 μmol) was added BH$_3$.THF (1.0 M in THF, 0.5 mL, 0.5 mmol) dropwise, and the reaction was stirred at 55° C. After 1 h, the reaction was cooled to room temperature, water (2 mL) was added dropwise and the solution was evaporated. The residue was taken up in a saturated aqueous NaHCO$_3$ solution and extracted with CH$_2$Cl$_2$. The organic layer was dried (MgSO$_4$) and concentrated in vacuo. The residue was purified by column chromatography (silica gel; 19:1, CH$_2$Cl$_2$/MeOH) to obtain 8 (70 mg, 46%) as a white powder: R$_f$ 0.27 (19:1, CH$_2$Cl$_2$/MeOH); $^1$H NMR (300 MHz, CDCl$_3$): δ 5.19-5.05 (m, 1H), 4.67-4.49 (m, 1H), 3.84 (dd, J=2.7, 12.4 Hz, 1H), 3.72 (s, 3H), 3.52 (dd, J=4.2, 12.4 Hz, 1H), 2.80-2.66 (m, 1H), 2.35-2.23 (m, 2H), 2.21-2.08 (m, 6H), 2.00 (dd, J=2.7, 11.5 Hz, 1H), 1.81-1.73 (m, 1H), 1.68-1.46 (m, 3H), 1.37 (s, 3H), 1.08 (s, 3H); $^{13}$C NMR (75 MHz, CDCl$_3$): δ 202.1, 171.6, 171.6, 170.0, 77.2, 75.1, 64.7, 64.0, 53.5, 52.0, 50.9, 42.1, 38.1, 37.4, 34.8, 30.7, 20.6, 18.1, 16.3, 15.2; HRMS-ESI (m/z): [M+H]$^+$ calcd for C$_{20}$H$_{28}$O$_8$, 397.1862; found, 397.1859.

Synthesis of Compound 9

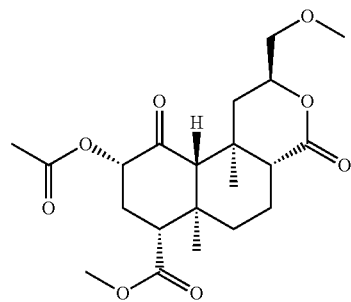

(9)

To a CH$_3$CN solution of 8 (20 mg, 52 μmol) was added Ag$_2$O (150 mg, 647 μmol) and iodomethane (70 μL, 1.1 mmol). The reaction was stirred at 60° C. (5 days). The reaction was concentrated and the residue purified by column chromatography (silica gel; 0-5% MeOH/CH$_2$Cl$_2$) followed by a second column (silica gel; 0-25% EtOAc/CH$_2$Cl$_2$, then 5% MeOH/CH$_2$Cl$_2$) to yield 9 (2.5 mg, 15%) as an orange resin: R$_f$ 0.50 (4:1, CH$_2$Cl$_2$/EtOAc); $^1$H NMR (300 MHz, CDCl$_3$): δ 5.13 (t, J=9.9 Hz, 1H), 4.68-4.53 (m, 1H), 3.79-3.53 (m, 4H), 3.49-3.29 (m, 4H), 2.81-2.67 (m, 1H), 2.39-2.24 (m, 2H), 2.24-2.06 (m, 6H), 2.05-1.96 (m, 1H), 1.84-1.70 (m, 1H), 1.69-1.47 (m, 3H), 1.35 (s, 3H), 1.08 (s, 3H); $^{13}$C NMR (75 MHz, CDCl$_3$): δ 202.1, 171.6, 171.5, 170.0, 76.0, 75.1, 74.0, 64.2, 59.3, 53.5, 52.0, 50.6, 42.1, 38.1, 37.8, 34.9, 30.7, 20.6, 18.1, 16.2, 15.1; HRMS-ESI (m/z): [M+H]$^+$ calcd for C$_{21}$H$_{30}$O$_8$, 411.2019, found, 411.2036.

Synthesis of Compound 10

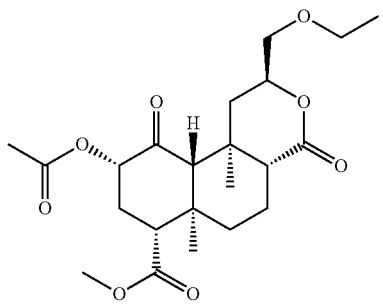

(10)

To a CH$_3$CN solution of 8 (16 mg, 40 μmol) was added Ag$_2$O (122 mg, 526 μmol) and iodoethane (94 μL, 1.2 mmol). The reaction was stirred at 60° C. (4 days). Additional Ag$_2$O (136 mg, 586 μmol) and iodoethane (94 μL, 1.2 mmol) were added. The reaction was stirred at room temperature (8 days) and then concentrated. The residue purified by column chromatography (silica gel; 0-5% MeOH/CH$_2$Cl$_2$) followed by a second column (silica gel; 0-20% EtOAc/CH$_2$Cl$_2$) to yield 10 (2.0 mg, 12%) as a clear resin: R$_f$ 0.50 (19:1, CH$_2$Cl$_2$/MeOH); $^1$H NMR (300 MHz, CDCl$_3$): δ 5.18-5.07 (m, 1H), 4.60 (d, J=5.8 Hz, 1H), 3.71 (d, J=5.1 Hz, 3H), 3.64-3.37 (m, 4H), 2.82-2.67 (m, 1H), 2.31 (d, J=10.2 Hz, 2H), 2.23-2.07 (m, 6H), 2.01 (d, J=8.4 Hz, 1H), 1.76 (dd, J=3.2, 9.8 Hz, 1H), 1.55 (d, J=14.6 Hz, 3H), 1.42-1.03 (m, 9H); $^{13}$C NMR (75 MHz, CDCl$_3$): δ 202.1, 171.6, 171.6, 170.0, 76.2, 75.1, 72.0, 67.1, 64.2, 53.5, 52.0, 50.7, 42.1, 38.1, 38.0, 34.9, 30.7, 20.6, 18.2, 16.2, 15.1, the OCH$_2$CH$_3$ signal was not detected; HRMS-ESI (m/z): [M+H]$^+$ calcd for C$_{22}$H$_{32}$O$_8$, 425.2175, found, 425.2168.

Synthesis of Compound 11

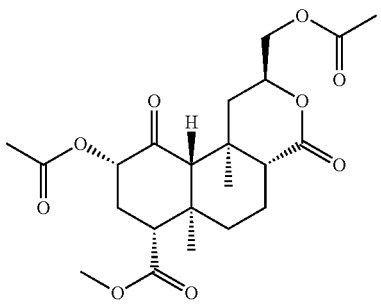

(11)

To a CH$_2$Cl$_2$ solution of 8 (19 mg, 48 μmol) was added Ac$_2$O (5.4 μL, 57 μmol) and Et$_3$N (8 μL, 57 μmol). The reaction was stirred at room temperature (25 h). DMAP (catalytic amount) was added and the reaction stirred for an additional 4 h. The reaction was concentrated and the residue purified by column chromatography (silica gel; 0-4% MeOH/CH$_2$Cl$_2$) to obtain 11 (17 mg, 79%) as a white foam: R$_f$ 0.35 (19:1, CH$_2$Cl$_2$/MeOH); $^1$HNMR (300 MHz, CDCl$_3$): δ 5.22-5.08 (m, 1H), 4.80-4.65 (m, 1H), 4.22 (dd, J=3.2, 12.1 Hz, 1H), 4.03 (dd, J=5.2, 12.1 Hz, 1H), 3.72 (s, 3H), 2.83-2.66 (m, 1H), 2.36-2.20 (m, 3H), 2.21-2.12 (m, 5H), 2.09 (s, 3H), 1.97 (dd, J=2.7, 11.7 Hz, 1H), 1.79 (dd, J=2.8, 9.8 Hz, 1H), 1.68-1.53 (m, 3H), 1.37 (s, 3H), 1.09 (s, 3H); $^{13}$C NMR (75 MHz, CDCl$_3$): δ 201.9, 171.5, 170.8, 170.6, 170.0, 75.0, 74.5, 65.9, 64.1, 53.5, 52.0, 51.1, 42.0, 38.2, 38.0, 34.9, 30.7, 20.8, 20.6, 18.1, 16.3, 15.0; HRMS-ESI (m/z): [M+H]$^+$ calcd for C$_{22}$H$_{30}$O$_9$, 439.1968; found, 439.1956.

Example 3

Syntheses of C-13 aryl and heteroaryl ketones (compounds 12-16)

C-13 aryl and heteroaryl ketones were prepared as described in Scheme 3.

Scheme 3

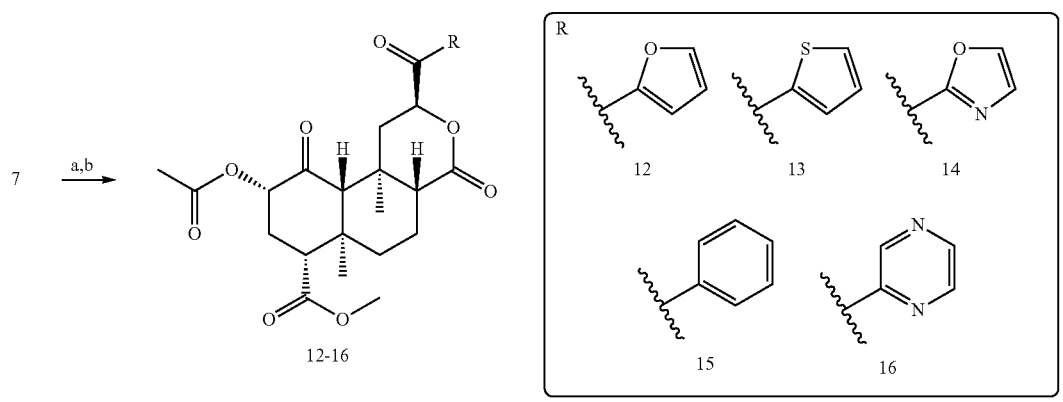

Scheme 3. Syntheses of C-13 aryl and heteroaryl ketones. Reagents and conditions: (a) (COCl)₂, CH₂Cl₂, r.t.; (b) RSn(nBu)₃, Pd(PPh₃)₄ toluene, 80-100° C., 7-57%, over two steps.

Synthesis of Compound 12

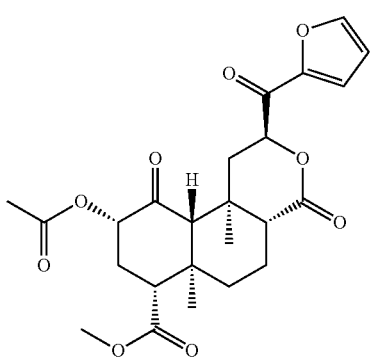

(12)

Compound 12 (7.3 mg, 33%) was prepared as a white powder from 7 (20 mg, 49 μmol), oxalyl chloride (1 mL, 2 mmol), Pd(PPh₃)₄ (catalytic amount), and 2-(tributylstannyl) furan (17 μL, 54 μmol). A solution of 7 in oxalyl chloride (2.0 M in CH₂Cl₂) was stirred at room temperature (3 h). The reaction solvent was evaporated and the crude was used immediately without purification for the Stille coupling reaction. The 2-(tributylstannyl)furan (1.1 equiv) was added to a mixture of crude acyl chloride and Pd(PPh₃)₄ in anhydrous toluene and the reaction was stirred at 80-100° C. (18 h). A saturated aqueous KF solution and Et₂O were added to the reaction mixture. The organic layer was dried (MgSO₄) and the residue purified by column chromatography to yield compound 12. Column chromatography (silica gel; 0-50% EtOAc/hexanes): $R_f$ 0.31 (1:1, hexanes/EtOAc); ¹H NMR (300 MHz, CDCl₃): δ 7.74-7.61 (m, 1H), 7.37 (dd, J=0.6, 3.6 Hz, 1H), 6.59 (dd, J=1.7, 3.6 Hz, 1H), 5.62 (t, J=8.3 Hz, 1H), 5.12 (t, J=10.0 Hz, 1H), 3.71 (s, 3H), 2.78-2.69 (m, 1H), 2.63 (dd, J=8.0, 13.6 Hz, 1H), 2.38-2.22 (m, 2H), 2.22-2.05 (m, 6H), 1.82-1.50 (m, 4H), 1.44 (s, 3H), 1.08 (s, 3H); ¹³C NMR (75 MHz, CDCl₃): δ 201.9, 184.0, 171.5, 170.7, 169.8, 149.9, 147.8, 120.3, 112.9, 76.0, 74.9, 64.6, 53.2, 51.9, 49.6, 42.0, 38.0, 37.7, 35.5, 30.7, 20.6, 18.2, 16.4, 16.0; HRMS-ESI (m/z): [M+NH₄]⁺ calcd for C₂₄H₂₈O₉, 478.2077; found, 478.2084.

Synthesis of Compound 13

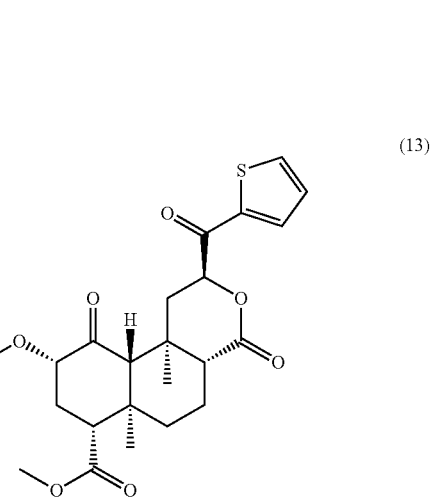

(13)

Compound 13 (8.8 mg, 36%) was prepared as a white powder from 7 (21 mg, 51 μmol), oxalyl chloride (1 mL, 2 mmol), Pd(PPh₃)₄ (catalytic amount), and 2-(tributylstannyl) thiophene (18 μL, 57 μmol) utilizing the method described above and stirring the reaction at 100° C. (2 h), and using column chromatography (silica gel; 0-33% acetone/hexanes) followed by a second column (silica gel; 0-10% EtOAc/ CH₂Cl₂): $R_f$ 0.21 (2:1, hexanes/acetone); ¹H NMR (300 MHz, CDCl₃): δ 7.82 (dd, J=1.1, 3.9 Hz, 1H), 7.75 (dd, J=1.1, 5.0 Hz, 1H), 7.18 (dd, J=3.9, 5.0 Hz, 1H), 5.62 (t, J=8.2 Hz, 1H), 5.21-5.04 (m, 1H), 3.71 (s, 3H), 2.78-2.68 (m, 1H), 2.62 (dd, J=8.1, 13.7 Hz, 1H), 2.34-2.23 (m, 2H), 2.23-2.06 (m, 6H), 1.81-1.53 (m, 4H), 1.44 (s, 3H), 1.08 (s, 3H); ¹³C NMR (75 MHz, CDCl₃): δ 202.1, 188.4, 171.7, 170.8, 170.0, 140.1, 136.0, 134.2, 128.9, 76.9, 75.0, 64.7, 53.4, 52.1, 49.7, 42.1, 38.6, 37.8, 35.6, 30.8, 20.7, 18.3, 16.8, 16.2; HRMS-ESI (m/z): [M+NH₄]⁺ calcd for C₂₄H₂₈O₈S, 494.1849; found, 494.1831.

Synthesis of Compound 14

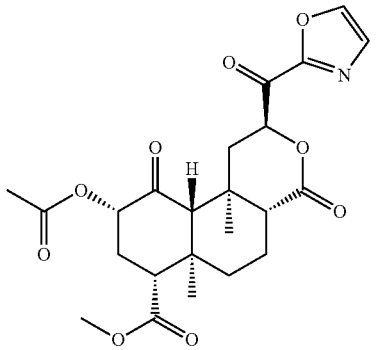

(14)

Compound 14 (3.1 mg, 6.5%) was prepared as a clear resin from 7 (21 mg, 52 μmol), oxalyl chloride (1 mL, 2 mmol), Pd(PPh$_3$)$_4$ (catalytic amount), and 2-(tributylstannyl)oxazole (12 μL, 57 μmol) utilizing the method described above and stirring the reaction at 100° C. (2 h), and using column chromatography (silica gel; 0-40% acetone/hexanes) followed by a second column (silica gel; 0-50% EtOAc/hexanes): R$_f$ 0.21 (2:1, hexanes/acetone); R$_f$ 0.09 (1:1, hexanes/EtOAc); $^1$H NMR (300 MHz, CDCl$_3$): δ 7.89 (d, J=0.6 Hz, 1H), 7.39 (d, J=0.6 Hz, 1H), 5.93 (dd, J=7.7, 10.0 Hz, 1H), 5.20-4.99 (m, 1H), 3.72 (s, 3H), 2.82-2.67 (m, 2H), 2.34-2.19 (m, 3H), 2.18-2.12 (m, 5H), 1.83-1.51 (m, 4H), 1.47 (s, 3H), 1.09 (s, 3H); $^{13}$C NMR (75 MHz, CDCl$_3$): δ 201.7, 183.2, 171.7, 170.4, 170.1, 142.8, 129.9, 77.4, 76.8, 75.0, 64.6, 53.5, 52.2, 50.0, 42.2, 38.3, 38.0, 35.8, 30.8, 20.8, 18.3, 16.2, 16.0; HRMS-ESI (m/z): [M+NH$_4$]$^+$ calcd for C$_{23}$H$_{27}$NO$_9$, 479.203; found, 479.2019.

Synthesis of Compound 15

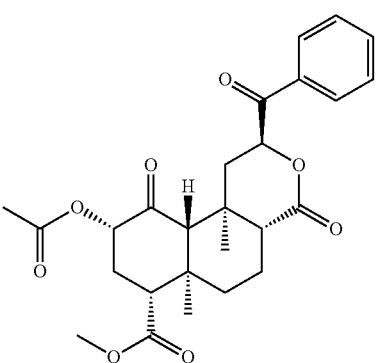

(15)

Compound 15 (20 2 mg, 59% yield) was prepared as a white powder from 7 (30 mg, 73 μmol), oxalyl chloride (1 mL, 2 mmol), Pd(PPh$_3$)$_4$ (catalytic amount), and 2-(tributylstannyl)phenyl (26 μL, 80 μmol) utilizing the method described above and stirring the reaction at 100° C. (2 h), and using column chromatography (silica gel; 0-33% acetone/hexanes): R$_f$ 0.29 (2:1, hexanes/acetone); $^1$H NMR (300 MHz, CDCl$_3$): δ 7.90 (dd, J=1.3, 8.4 Hz, 2H), 7.68-7.57 (m, 1H), 7.55-7.43 (m, 2H), 5.87 (t, J=8.3 Hz, 1H), 5.15-5.03 (m, 1H), 3.70 (s, 3H), 2.76-2.59 (m, 2H), 2.34-2.22 (m, 2H), 2.21-2.06 (m, 6H), 1.82-1.52 (m, 4H), 1.44 (s, 3H), 1.06 (s, 3H); $^{13}$C NMR (75 MHz, CDCl$_3$): δ 202.0, 195.2, 171.6, 171.0, 169.8, 134.3, 133.3, 129.1, 128.9, 75.2, 74.8, 64.6, 53.1, 51.9, 49.2, 41.9, 38.2, 37.6, 35.5, 30.6, 20.6, 18.2, 16.7, 16.0; HRMS-ESI (m/z): [M+NH$_4$]$^+$ calcd for C$_{26}$H$_{30}$O$_8$, 488.2284; found, 488.2297.

Synthesis of Compound 16

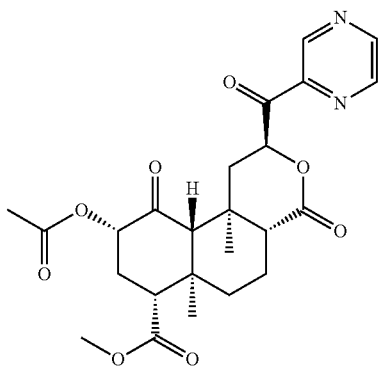

(16)

Compound 16 (19.9 mg, 57% yield) was prepared as an off-white powder from 7 (30 mg, 73 μmol), oxalyl chloride (1 mL, 2 mmol), Pd(PPh$_3$)$_4$ (catalytic amount), and 2-(tributylstannyl)pyrazine (26 μL, 81 μmol) utilizing the method described above and stirring the reaction at 100° C. (2 h), and using column chromatography (silica gel; 0-40% acetone/hexanes): R$_f$ 0.08 (2:1, hexanes/acetone); $^1$H NMR (300 MHz, CDCl$_3$): δ 9.24 (d, J=1.4 Hz, 1H), 8.80 (d, J=2.4 Hz, 1H), 8.72-8.59 (m, 1H), 6.28 (dd, J=8.3, 9.2 Hz, 1H), 5.16-4.97 (m, 1H), 3.70 (s, 3H), 2.81 (dd, J=8.1, 13.3 Hz, 1H), 2.75-2.66 (m, 1H), 2.32-2.21 (m, 2H), 2.21-2.09 (m, 6H), 1.81-1.53 (m, 3H), 1.49-1.35 (m, 4H), 1.07 (s, 3H); $^{13}$C NMR (75 MHz, CDCl$_3$): δ 202.0, 196.1, 171.8, 171.1, 170.1, 149.0, 145.3, 144.9, 144.1, 75.9, 75.0, 64.8, 53.5, 52.3, 49.9, 42.2, 38.5, 38.0, 35.9, 30.9, 20.9, 18.5, 16.3, 16.2; HRMS-ESI (m/z): [M+NH$_4$]$^+$ calcd for C$_{24}$H$_{28}$N$_2$O$_8$, 490.2189; found, 490.2209.

Example 4

Syntheses of C-13 aryl and heteroaryl alcohols (compound 17)

C-13 aryl and heteroaryl alcohols were prepared as described in Scheme 4.

Scheme 4

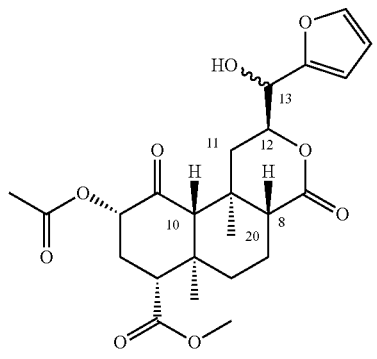

Scheme 4. Syntheses of C-13 aryl and heteroaryl alcohols. Reagents and conditions: (c) NaBH$_4$, CH$_3$OH, 0° C., 19%.

Synthesis of Compound 17

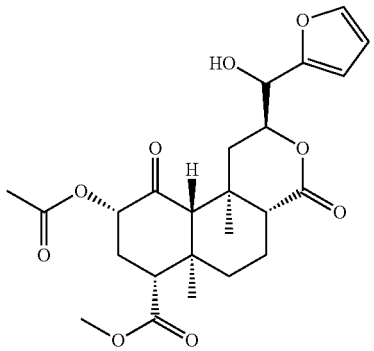

To a MeOH solution of 12 (82 mg, 178 μmol) was added NaBH$_4$ (5.8 mg, 153 μmol) and the reaction was stirred at 0° C. (1.5 h), concentrated and the residue purified by column chromatography (silica gel; 0-4% MeOH/CH$_2$Cl$_2$) followed by a second column (silica gel, 0-40% EtOAc/CH$_2$Cl$_2$) and a third column (silica gel, 0-50% EtOAc/hexanes) to yield 17 (14 mg, 19% BOSM) as a clear resin and as a ~1:1 mixture of 13-epimers: R$_f$ 0.16 (4:1, CH2Cl$_2$/EtOAc); $^1$H NMR (300 MHz, CDCl$_3$): δ 7.43-7.35 (m, 2H), 6.44-6.27 (m, 4H), 5.13 (dd, J=8.6, 11.3 Hz, 2H), 4.94-4.76 (m, 3H), 4.61 (br s, 1H), 3.71 (d, J=2.6 Hz, 6H), 2.80-2.64 (m, 2H), 2.38-2.22 (m, 4H), 2.21-2.04 (m, 12H), 1.99 (dd, J=3.1, 10.7 Hz, 1H), 1.89 (dd, J=3.0, 11.2 Hz, 1H), 1.81-1.69 (m, 2H), 1.66-1.47 (m, 6H), 1.43-1.23 (m, 8H), 1.07 (d, J=3.9 Hz, 6H); $^{13}$C NMR (75 MHz, CDCl$_3$): δ 201.9, 201.9, 171.6, 171.5, 171.4, 171.0, 169.9, 169.8, 151.8, 151.4, 142.6, 142.6, 110.5, 110.5, 108.3, 108.2, 78.7, 78.2, 77.2, 74.9, 74.9, 70.2, 69.7, 64.1, 53.5, 53.4, 52.0, 51.9, 50.9, 50.6, 42.0, 42.0, 38.3, 38.3, 38.0, 38.0, 34.9, 34.7, 30.8, 30.8, 20.6, 20.6, 18.1, 16.2, 16.2, 15.2, 15.1, one signal was not detected; HRMS-ESI (m/z): [M+H]$^+$ calcd for C$_{24}$H$_{30}$O$_9$, 463.1968; found, 463.1971.

Example 5

Syntheses of C-13 esters and amides (compounds 18-27)

C-13 esters and amides were prepared as described in Scheme 5.

Synthesis of Compound 18

To a toluene (3 mL)/MeOH (2 mL) solution of 7 (21 mg, 51 μmol) was added TMSCHN$_2$ (36 μL, 72 μmol) dropwise. The solution was stirred at room temperature (45 min), concentrated, and the residue purified by column chromatography (silica gel; 1:1, EtOAc/hexanes) to obtain 18 (10 mg, 48%) as a white powder: R$_f$ 0.31 (1:1, hexanes/EtOAc); $^1$H NMR (300 MHz, CDCl$_3$): δ 5.19-5.08 (m, 1H), 4.98 (dd, J=7.3, 9.7 Hz, 1H), 3.77 (s, 3H), 3.72 (s, 3H), 2.78-2.69 (m, 1H), 2.61 (dd, J=7.3, 13.6 Hz, 1H), 2.35-2.24 (m, 2H), 2.17 (s, 3H), 2.16-2.06 (m, 3H), 1.81-1.73 (m, 1H), 1.71-1.48 (m, 3H), 1.36 (s, 3H), 1.07 (s, 3H); $^{13}$C NMR (75 MHz, CDCl$_3$): δ 201.7, 171.5, 170.5, 170.0, 169.9, 74.9, 73.6, 64.3, 53.4, 52.9, 52.0, 50.0, 42.0, 38.9, 37.8, 35.2, 30.6, 20.6, 18.1, 16.1, 15.8; HRMS-ESI (m/z): [M+NH$_4$]$^+$ calcd for C$_{21}$H$_{28}$O$_9$, 442.2077; found, 442.2088.

Synthesis of Compound 19

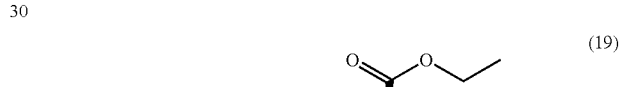

Compound 19 (5.1 mg, 49%) was prepared as a white powder from 7 (26 mg, 63 μmol), EDCI (14 mg, 73 μmol),

Scheme 5

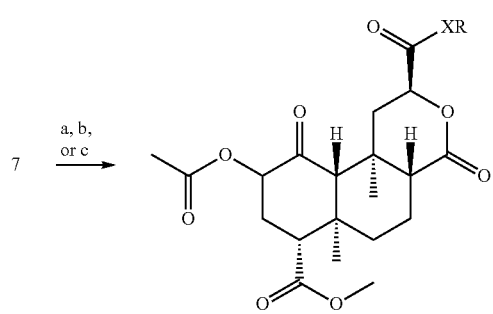

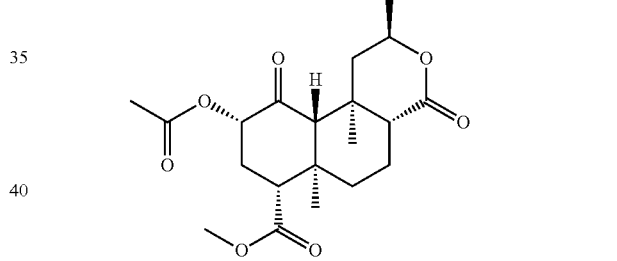

Scheme 5. Syntheses of C-13 esters and amides. Reagents and conditions: (a) TMSCHN$_2$, CH$_3$OH, toluene, r.t., 48%; (b) ROH, EDCI, DMAP, CH$_2$Cl$_2$, r.t., 26-54%; (c) RNH$_2$, EDCI, HOBt, CH$_2$Cl$_2$, r.t., 45-72%.

DMAP (catalytic amount), and EtOH (7.4 µL, 127 µmol). To a solution of 7, EDCI (1.2 equiv), and DMAP (catalytic amount) in $CH_2Cl_2$ was added the EtOH (2.0 equiv). The reaction was stirred at room temperature (3 h). The reaction was washed with an aq 1M HCl solution, brine, dried ($MgSO_4$), and concentrated in vacuo. The residue was purified by column chromatography (silica gel; 1:1, EtOAc/hexanes): $R_f$ 0.63 (1:1, hexanes/EtOAc); $^1$H NMR (300 MHz, $CDCl_3$): δ 5.21-5.07 (m, 1H), 4.95 (dd, J=7.2, 9.7 Hz, 1H), 4.33-4.14 (m, 2H), 3.72 (s, 3H), 2.79-2.68 (m, 1H), 2.60 (dd, J=7.2, 13.5 Hz, 1H), 2.38-2.23 (m, 2H), 2.18 (s, 3H), 2.16-2.06 (m, 3H), 1.79-1.74 (m, 1H), 1.72-1.47 (m, 3H), 1.36 (s, 3H), 1.29 (t, J=7.1 Hz, 3H), 1.08 (s, 3H); $^{13}$C NMR (75 MHz, $CDCl_3$): δ 201.7, 171.5, 170.1, 170.1, 169.9, 74.9, 73.8, 64.4, 62.1, 53.4, 52.0, 50.0, 42.0, 38.9, 37.8, 35.2, 30.7, 20.6, 18.1, 16.1, 15.8, 14.1; HRMS-ESI (m/z): $[M+NH_4]^+$ calcd for $C_{22}H_{30}O_9$, 456.2234; found, 456.2246.

Synthesis of Compound 20

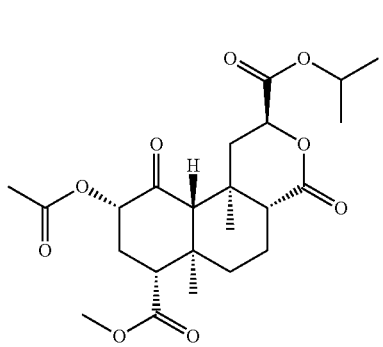

(20)

Compound 20 (19 mg, 38%) was prepared as a clear resin from 7 (25 mg, 60 µmol), EDCI (15 mg, 78 µmol), DMAP (catalytic amount), and i-PrOH (9 µL, 118 µmol) utilizing the methodology described above and purified using column chromatography (silica gel; 1:2, EtOAc/hexanes): $R_f$ 0.45 (1:1, hexanes/EtOAc); $^1$H NMR (300 MHz, $CDCl_3$): δ 5.20-5.11 (m, 1H), 5.11-4.99 (m, 1H), 4.91 (dd, J=7.2, 9.8 Hz, 1H), 3.72 (s, 3H), 2.78-2.69 (m, 1H), 2.57 (dd, J=7.1, 13.5 Hz, 1H), 2.34-2.29 (m, 2H), 2.17 (s, 3H), 2.17-2.06 (m, 3H), 1.80-1.71 (m, 1H), 1.71-1.46 (m, 3H), 1.36 (s, 3H), 1.27 (d, J=6.7 Hz, 3H), 1.26 (d, J=6.7 Hz, 3H), 1.08 (s, 3H); $^{13}$C NMR (75 MHz, $CDCl_3$): δ 201.8, 171.5, 170.2, 169.9, 169.6, 74.8, 74.0, 70.0, 64.3, 53.3, 52.0, 50.1, 42.0, 38.9, 37.8, 35.2, 30.7, 21.6, 21.6, 20.6, 18.1, 16.1, 15.8; HRMS-ESI (m/z): $[M+NH_4]^+$ calcd for $C_{23}H_{32}O_9$, 470.2390; found, 470.2404.

Synthesis of Compound 21

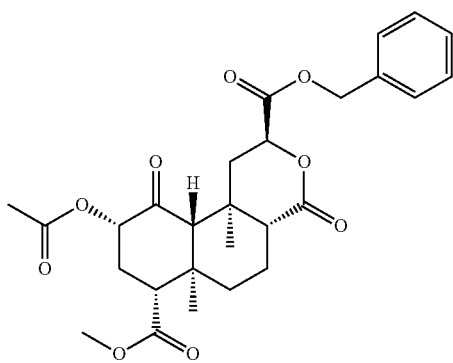

(21)

Compound 21 (14 mg, 54%) was prepared as a clear resin from 7 (21 mg, 50 µmol), EDCI (12 mg, 63 µmol), DMAP (catalytic amount) and benzyl alcohol (11 µL, 101 µmol) utilizing the methodology described above and purified using column chromatography (silica gel; 1:2, EtOAc/hexanes): $R_f$ 0.29 (1:1, hexanes/EtOAc); $^1$H NMR (300 MHz, $CDCl_3$): δ 7.44-7.33 (m, 5H), 5.20 (dd, J=12.0, 27.9 Hz, 2H), 5.14-5.05 (m, 1H), 4.99 (dd, J=7.6, 8.7 Hz, 1H), 3.72 (s, 3H), 2.71-2.63 (m, 1H), 2.59 (dd, J=7.6, 13.7 Hz, 1H), 2.32-2.22 (m, 2H), 2.17 (s, 3H), 2.11-1.97 (m, 3H), 1.78-1.68 (m, 1H), 1.66-1.43 (m, 3H), 1.34 (s, 3H), 1.05 (s, 3H); $^{13}$C NMR (75 MHz, $CDCl_3$): δ 201.7, 171.5, 170.2, 170.0, 169.9, 134.8, 128.8, 128.8, 128.7, 74.8, 73.6, 67.6, 64.5, 53.3, 52.0, 49.7, 41.9, 38.9, 37.7, 35.2, 30.6, 20.6, 18.1, 16.3, 16.1; HRMS-ESI (m/z): $[M+NH_4]^+$ calcd for $C_2H_{32}O_9$, 518.2390; found, 518.2407.

Synthesis of Compound 22

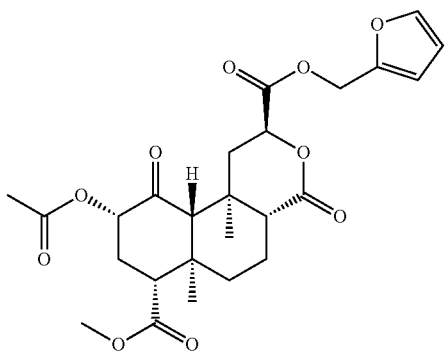

(22)

Compound 22 (7.8 mg, 26%) was prepared as a white powder from 7 (25 mg, 61 µmol), EDCI (14 mg, 75 µmol), DMAP (catalytic amount), and furfuryl alcohol (11 µL, 121 µmol) utilizing the methodology described above and purified using column chromatography (silica gel; 1:2, EtOAc/hexanes): $R_f$ 0.37 (1:1, hexanes/EtOAc); $^1$H NMR (300 MHz, $CDCl_3$): δ 7.44 (dd, J=0.8, 1.9 Hz, 1H), 6.45 (dd, J=0.6, 3.3 Hz, 1H), 6.38 (dd, J=1.9, 3.3 Hz, 1H), 5.24-5.06 (m, 3H), 4.98 (dd, J=7.4, 9.2 Hz, 1H), 3.72 (s, 3H), 2.76-2.67 (m, 1H), 2.59 (dd, J=7.4, 13.7 Hz, 1H), 2.34-2.23 (m, 2H), 2.17 (s, 3H), 2.14-2.04 (m, 3H), 1.79-1.71 (m, 1H), 1.70-1.48 (m, 3H), 1.34 (s, 3H), 1.06 (s, 3H); $^{13}$C NMR (75 MHz, $CDCl_3$): δ 201.7, 171.5, 170.1, 169.9, 169.8, 148.3, 143.7, 111.6, 110.7, 74.8, 73.6, 64.4, 59.2, 53.4, 52.0, 49.9, 41.9, 38.9, 37.8, 35.2, 30.7, 20.6, 18.1, 16.1, 16.1; HRMS-ESI (m/z): $[M+N11_4]^+$ calcd for $C_{25}H_{30}O_{10}$, 508.2183; found, 508.2161.

Synthesis of Compound 23

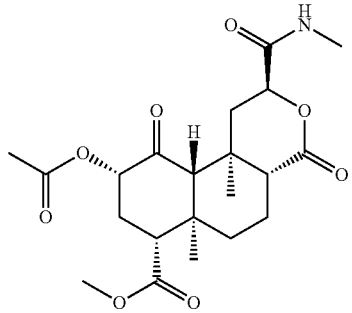

(23)

Compound 23 (15 mg, 70%) was prepared as a clear resin from 7 (21 mg, 50 µmol), EDCI (12 mg, 61 µmol), HOBt (7.9 mg, 59 µmol), and $CH_3NH_2$ (2.0 M in $CH_2Cl_2$, 36 µL, 72

µmol). To a CH₂Cl₂ solution of 7, EDCI (1.2 equiv), and HOBt (1.2 equiv) was added the methylamine (1.5 equiv) and the solution was stirred at room temperature (5-20 min). The reaction was washed with H₂O, dried (MgSO₄), and concentrated in vacuo. The residue was purified by column chromatography (silica gel; 19:1, CH₂Cl₂/MeOH): $R_f$ 0.08 (19:1, CH₂Cl₂/CH₃OH); ¹H NMR (300 MHz, CDCl₃): δ 6.43 (br d, J=4.6 Hz, 1H), 5.15 (dd, J=8.4, 11.5 Hz, 1H), 4.89 (dd, J=6.3, 10.6 Hz, 1H), 3.71 (s, 3H), 2.83 (d, J=4.9 Hz, 3H), 2.77-2.65 (m, 2H), 2.35-2.21 (m, 2H), 2.16 (s, 3H), 2.04-2.16 (m, 2H), 2.00 (dd, J=2.8, 11.3 Hz, 1H), 1.65 (ddd, J=10.7, 24.2, 24.9 Hz, 4H), 1.37 (s, 3H), 1.08 (s, 3H); ¹³C NMR (75 MHz, CDCl₃): δ 201.4, 171.5, 170.3, 169.8, 169.6, 75.8, 74.7, 64.0, 53.4, 52.0, 51.0, 41.9, 39.1, 37.8, 35.3, 30.8, 26.0, 20.6, 18.1, 16.3, 15.5; HRMS-ESI (m/z): [M+NH₄]⁺ calcd for C₂₁H₂₉NO₈, 441.2237; found, 441.2245.

Synthesis of Compound 24

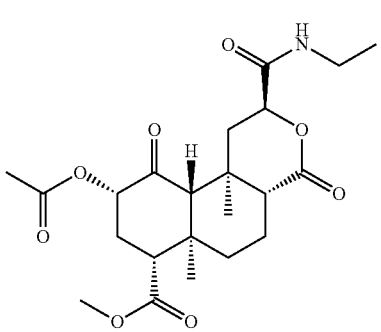

(24)

Compound 24 (11 mg, 51%) was prepared as a black resin from 7 (21 mg, 51. µmol), EDCI (12 mg, 61.1 µmol), HOBt (8.1 mg, 60 µmol), and EtNH₂ (2.0 M in THF, 64 µL, 0.13 mmol) utilizing the methodology described above and purified using column chromatography (silica gel; 19:1, CH₂Cl₂/MeOH): $R_f$ 0.26 (19:1, CH₂Cl₂/CH₃OH); ¹H NMR (300 MHz, CDCl₃): δ 6.38 (br s, 1H), 5.15 (dd, J=8.6, 11.7 Hz, 1H), 4.88 (dd, J=6.2, 10.8 Hz, 1H), 3.71 (s, 3H), 3.40-3.20 (m, 2H), 2.78-2.65 (m, 2H), 2.36-2.21 (m, 2H), 2.19-2.05 (m, 5H), 2.01 (dd, J=2.9, 11.5 Hz, 1H), 1.83-1.73 (m, 1H), 1.72-1.49 (m, 3H), 1.38 (s, 3H), 1.14 (t, J=7.3 Hz, 3H), 1.09 (s, 3H); ¹³C NMR (75 MHz, CDCl₃): δ 201.4, 171.5, 170.4, 169.6, 169.0, 75.8, 74.7, 64.0, 53.4, 52.0, 51.0, 41.9, 39.1, 37.8, 35.3, 34.2, 30.8, 20.6, 18.1, 16.3, 15.5, 14.7; HRMS-ESI (m/z): [M+NH₄]⁺ calcd for C₂₂H₃₁NO₈, 455.2393; found, 455.2380.

Synthesis of Compound 25

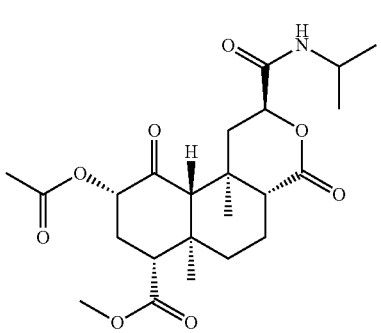

(25)

Compound 25 (16 mg, 69%) was prepared as a white powder from 7 (21 mg, 51 µmol), EDCI (12 mg, 63 µmol), HOBt (8.0 mg, 59 µmol), and i-PrNH₂ (6.4 µL, 75 µmol) utilizing the methodology described above and purified using column chromatography (silica gel; 1:1, EtOAc/hexanes): $R_f$ 0.11 (1:1, hexanes/EtOAc); ¹H NMR (300 MHz, CDCl₃): δ 6.20 (br d, J=8.0 Hz, 1H), 5.15 (dd, J=8.6, 11.6 Hz, 1H), 4.85 (dd, J=6.0, 10.9 Hz, 1H), 4.17-3.99 (m, 1H), 3.71 (s, 3H), 2.80-2.61 (m, 2H), 2.37-2.20 (m, 2H), 2.19-2.06 (m, 5H), 2.02 (dd, J=2.3, 11.4 Hz, 1H), 1.83-1.46 (m, 4H), 1.37 (s, 3H), 1.20-1.11 (m, 6H), 1.09 (s, 3H); ¹³C NMR (75 MHz, CDCl₃): δ 201.4, 171.5, 170.4, 169.6, 168.2, 75.9, 74.7, 63.9, 53.4, 52.0, 51.0, 41.9, 41.4, 39.2, 37.9, 35.3, 30.8, 22.6, 22.5, 20.6, 18.1, 16.3, 15.4; HRMS-ESI (m/z): [M+NH₄]⁺ calcd for C₂₃H₃₃NO₈, 469.2544; found, 469.2646.

Synthesis of Compound 26

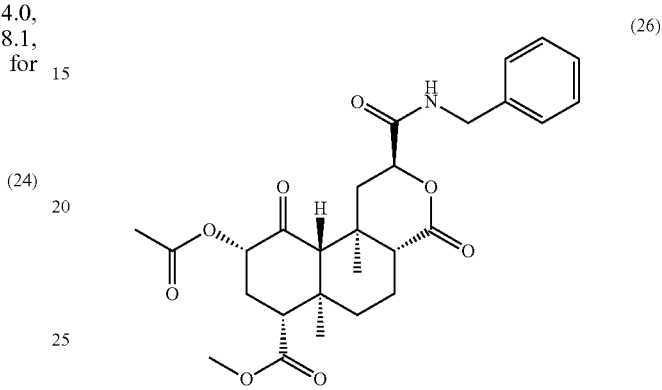

(26)

Compound 26 (17 mg, 72%) was prepared as a white powder from 7 (20 mg, 49 µmol), EDCI (12 mg, 62 µmol), HOBt (8.0 mg, 59 µmol), and benzylamine (8.0 µL, 73 µmol) utilizing method C, stirring at room temperature (5 min), and using column chromatography (silica gel; 1:1, EtOAc/hexanes): $R_f$ 0.22 (1:1, hexanes/EtOAc); ¹H NMR (300 MHz, CDCl₃): δ 7.42-7.19 (m, 5H), 6.76 (br t, J=5.6 Hz, 1H), 5.16 (dd, J=8.4, 11.6 Hz, 1H), 4.91 (dd, J=6.1, 10.8 Hz, 1H), 4.43 (d, J=5.9 Hz, 2H), 3.71 (s, 3H), 2.72 (dd, J=5.5, 12.8 Hz, 2H), 2.34-2.21 (m, 2H), 2.18-2.02 (m, 5H), 1.99 (dd, J=2.9, 11.2 Hz, 1H), 1.80-1.70 (m, 1H), 1.68-1.49 (m, 3H), 1.36 (s, 3H), 1.08 (s, 3H); ¹³C NMR (75 MHz, CDCl₃): δ 201.4, 171.5, 170.3, 169.6, 169.1, 137.4, 128.8, 127.9, 127.8, 75.9, 74.7, 63.9, 53.4, 51.9, 51.0, 43.3, 41.8, 39.2, 37.8, 35.3, 30.8, 20.6, 18.0, 16.3, 15.5; HRMS-ESI (m/z): [M+NH₄]⁺ calcd for C₂₇H₃₃NO₈, 517.2550; found, 517.2567.

Synthesis of Compound 27

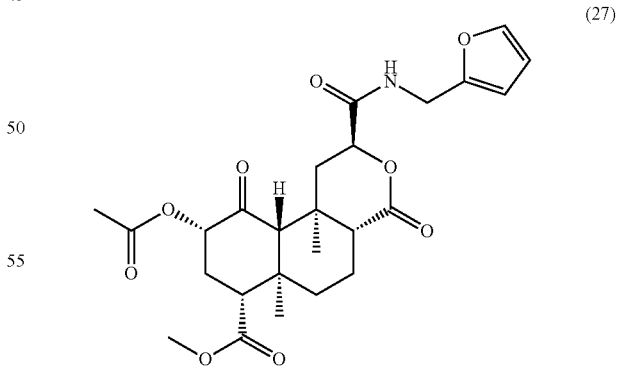

(27)

Compound 27 (11. mg, 45%) was prepared as a white powder from 7 (21 mg, 51 µmol), EDCI (12 mg, 62 µmol), HOBt (7.9 mg, 59 µmol), and furfurylamine (7.0 µL, 76 µmol) utilizing method C, stirring at room temperature (20 min), and using column chromatography (silica gel; 19:1, CH₂Cl₂/MeOH) followed by a second column (silica gel; 2:1, CH₂Cl₂/EtOAc): $R_f$ 0.26 (2:1, CH₂Cl₂/EtOAc); ¹H NMR (300 MHz, CDCl₃): δ 7.35 (dd, J=0.8, 1.8 Hz, 1H), 6.71 (br t, J=5.6 Hz, 1H), 6.32 (dd, J=1.9, 3.2 Hz, 1H), 6.23 (d, J=3.2 Hz, 1H), 5.15 (dd, J=8.5, 11.6 Hz, 1H), 4.91 (dd, J=6.2, 10.8 Hz, 1H), 4.51-4.36 (m, 2H), 3.71 (s, 3H), 2.78-2.65 (m, 2H), 2.35-2.21 (m, 2H), 2.20-1.96 (m, 6H), 1.82-1.72 (m, 1H), 1.70-1.50 (m, 3H), 1.37 (s, 3H), 1.08 (s, 3H); $^{13}$C NMR (75 MHz, CDCl$_3$): δ 201.4, 171.5, 170.2, 169.6, 169.0, 150.2, 142.5, 110.5, 108.0, 75.8, 74.7, 63.9, 53.4, 52.0, 51.0, 41.8, 39.1, 37.8, 36.2, 35.3, 30.8, 20.6, 18.0, 16.3, 15.5; HRMS-ESI (m/z): [M+NH$_4$]$^+$ calcd for C$_{25}$H$_{31}$NO$_9$, 507.2343; found, 507.2350.

Example 6

Syntheses of C-13 oxadiazoles (compounds 28a-34a and 28b-34b)

C-13 oxadiazoles were prepared as described in Scheme 6.

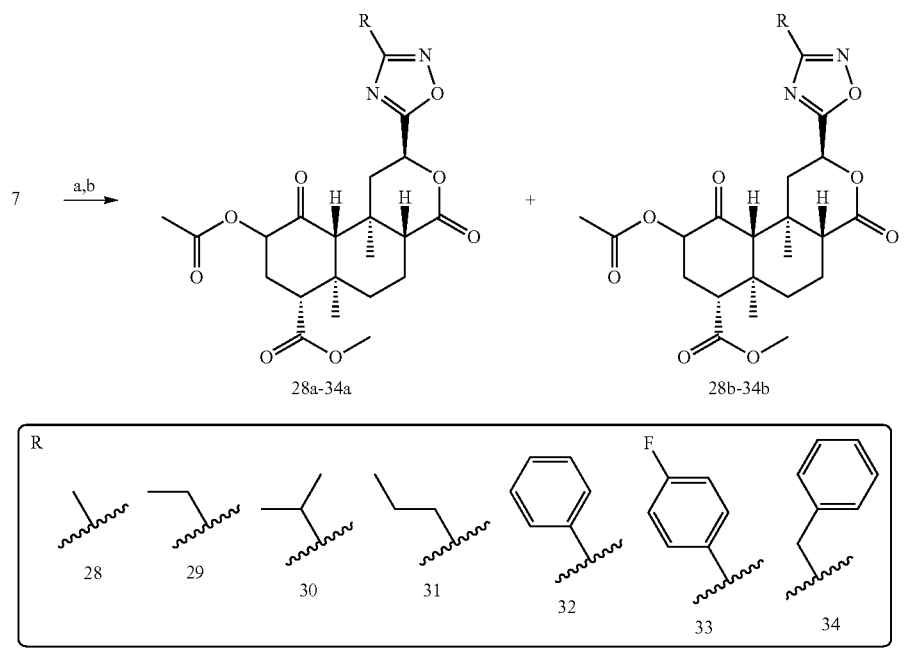

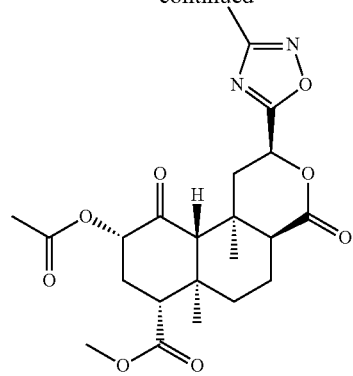

Scheme 6. Syntheses of C-13 oxadiazoles. Reagents and conditions: (a) RC(=NOH)NH2, EDCI, HOBt, CH2Cl2, r.t.; (b) toluene, 110° C., 10-45%, over two steps.

Synthesis of Compounds 28a and 28b

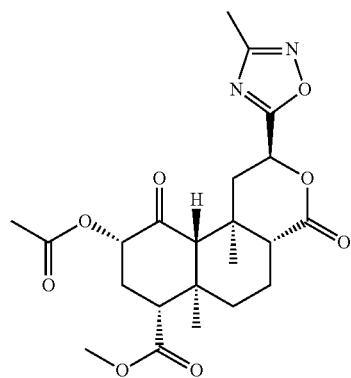

Compound 28a (3.6 mg, 8%) was prepared as a clear resin from 7 (43 mg, 105 µmol), EDCI (25 mg, 130 µmol), HOBt (19 mg, 142 µmol), and acetamide oxime (12 mg, 157 µmol). A mixture of 7, EDCI (1.2 equiv), and HOBt (1.3 equiv) in CH$_2$Cl$_2$ was stirred at room temperature. After 5 minutes, the acetamide oxime was added and the reaction stirred at room temperature. Upon completion, the reaction was washed with a saturated aq NaHCO$_3$ solution and brine. The organic layer was dried (MgSO$_4$) and concentrated to give the crude ester. Toluene was added and the solution was refluxed (17-43 h), concentrated, and the crude residue was purified by HPLC (silica gel, 20-55% EtOAc/hexanes): R$_f$ 0.32 (1:1, hexanes/EtOAc); HRMS-ESI (m/z): [M+H]$^+$ calcd for C$_{22}$H$_{28}$N$_2$O$_8$, 449.1924; found, 449.1907.

Compound 28b (5.9 mg, 13%) was also isolated as a clear resin: R$_f$ 0.23 (1:1, hexanes/EtOAc); $^1$H NMR (300 MHz, CDCl$_3$): δ 5.49 (dd, J=2.1, 12.1 Hz, 1H), 5.16-5.05 (m, 1H), 3.71 (s, 3H), 2.75 (dd, J=6.5, 10.3 Hz, 1H), 2.53 (dd, J=2.4, 15.1 Hz, 1H), 2.47-2.43 (m, 1H), 2.41 (s, 3H), 2.33-2.18 (m, 4H), 2.15 (s, 3H), 1.97 (dd, J=2.7, 13.3 Hz, 1H), 1.93-1.84 (m, 1H), 1.78 (dd, J=12.2, 15.1 Hz, 1H), 1.66 (s, 3H), 1.62-1.51 (m, 1H), 1.09 (s, 3H); HRMS-ESI (m/z): [M+H]$^+$ calcd for $C_{22}H_{28}N_2O_8$, 449.1924; found, 449.1920.

Synthesis of Compounds 29a

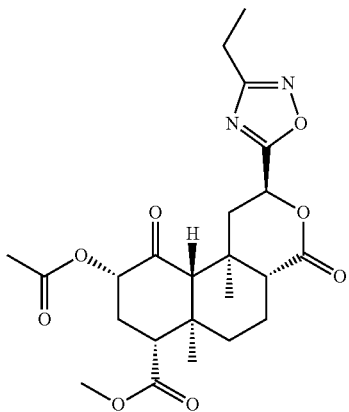

(29a)

Compound 29a (4.9 mg, 10%) was prepared as a white resin from 7 (43 mg, 104 μmol), EDCI (25 mg, 131 μmol), HOBt (20 mg, 144 μmol), and N-hydroxypropionamidine (12 μL, 146 μmol) in $CH_2Cl_2$ (2.4 mL) utilizing the methodology above and stirring at room temperature (42 h), and purified by HPLC (silica gel, 20-50% EtOAc/hexanes): $R_f$ 0.38 (1:1, hexanes/EtOAc); $^1$H NMR (300 MHz, $CDCl_3$): δ 5.73 (dd, J=6.3, 11.0 Hz, 1H), 5.21-5.06 (m, 1H), 3.73 (s, 3H), 2.82-2.71 (m, 3H), 2.64 (dd, J=6.3, 13.5 Hz, 1H), 2.36-2.20 (m, 4H), 2.20-2.13 (m, 4H), 1.91 (dd, J=11.3, 13.4 Hz, 1H), 1.85-1.77 (m, 1H), 1.72-1.52 (m, 2H), 1.46 (s, 3H), 1.32 (t, J=7.6 Hz, 3H), 1.11 (s, 3H); $^{13}$C NMR (75 MHz, $CDCl_3$): δ 201.7, 175.6, 171.8, 171.4, 169.9, 169.3, 74.9, 69.6, 63.9, 53.4, 52.0, 50.8, 42.0, 39.9, 37.9, 35.4, 30.6, 20.6, 19.7, 18.0, 16.3, 15.4, 11.3; HRMS-ESI (m/z): [M+H]$^+$ calcd for $C_{23}H_{30}N_2O_8$, 463.2080; found, 463.2089.

Synthesis of Compounds 30a and 30b

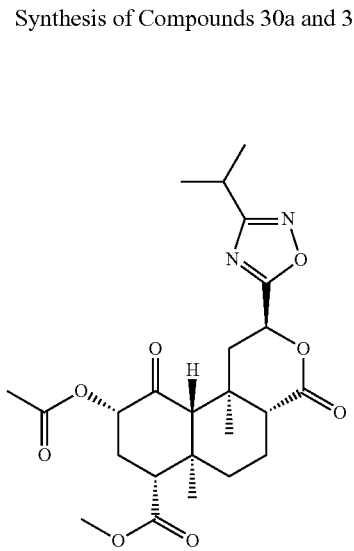

(30a)

(30b)

-continued

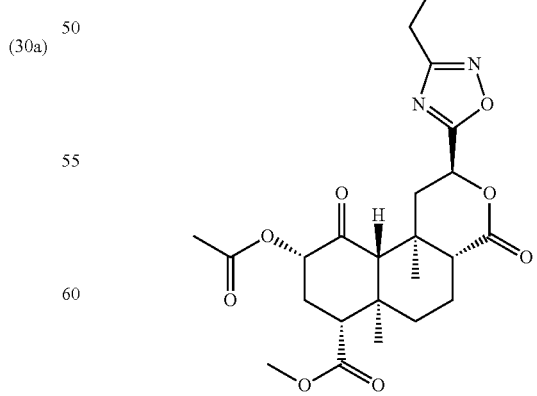

Compound 30a (20 mg, 41%) was prepared as a clear resin from 7 (42 mg, 102 μmol), EDCI (25 mg, 129 μmol), HOBt (20 mg, 146 μmol), and N-hydroxy 2-methylpropionamide (15 mg, 149 μmol) utilizing the methodology above and stirring at room temperature (19 h), and purified by HPLC (silica gel, 20-50% EtOAc/hexanes): $R_f$ 0.48 (1:1, hexanes/EtOAc); $^1$H NMR (300 MHz, $CDCl_3$): δ 5.73 (dd, J=6.1, 11.1 Hz, 1H), 5.18-5.09 (m, 1H), 3.72 (s, 3H), 3.17-3.02 (m, 1H), 2.80-2.69 (m, 1H), 2.62 (dd, J=6.1, 13.5 Hz, 1H), 2.36-2.22 (m, 4H), 2.21-2.12 (m, 4H), 1.91 (dd, J=11.4, 13.3 Hz, 1H), 1.85-1.76 (m, 1H), 1.75-1.52 (m, 2H), 1.46 (s, 3H), 1.33 (dd, J=0.6, 7.0 Hz, 6H), 1.11 (s, 3H); $^{13}$C NMR (75 MHz, $CDCl_3$): δ 201.7, 175.4, 175.3, 171.4, 169.9, 169.0, 74.9, 69.7, 63.8, 53.4, 52.0, 50.9, 41.9, 39.9, 37.9, 35.4, 30.6, 26.7, 20.5, 20.4, 20.4, 18.0, 16.3, 15.3; HRMS-ESI (m/z): [M+H]$^+$ calcd for $C_{24}H_{32}N_2O_8$, 477.2237; found, 477.2214.

Compound 30b (2.0 mg, 4%) was also isolated as a clear resin: $R_f$ 0.52 (1:1, hexanes/EtOAc); $^1$H NMR (300 MHz, $CDCl_3$): δ 5.50 (dd, J=2.4, 12.2 Hz, 1H), 5.19-5.05 (m, 1H), 3.71 (s, 3H), 3.20-3.02 (m, 1H), 2.75 (dd, J=5.7, 11.1 Hz, 1H), 2.53 (dd, J=2.1, 15.2 Hz, 1H), 2.47-2.41 (m, 1H), 2.34-2.17 (m, 4H), 2.15 (s, 3H), 1.97 (dd, J=3.1, 12.9 Hz, 1H), 1.93-1.84 (m, 1H), 1.78 (dd, J=12.6, 15.0 Hz, 1H), 1.66 (s, 3H), 1.61-1.52 (m, 1H), 1.33 (d, J=7.0 Hz, 6H), 1.09 (s, 3H); (HRMS-ESI (m/z): [M+H]$^+$ calcd for $C_{24}H_{32}N_2O_8$, 477.2237; found, 477.2249.

Synthesis of Compounds 31a (31a)

Compound 31a (9.6 mg, 21%) was prepared as a white powder from 7 (40 mg, 97 μmol), EDCI (24 mg, 125 μmol), HOBt (19 mg, 141 μmol), and N-hydroxy-butyramidine (17 mL, 146 µmol) utilizing methodology above and stirring at room temperature (18 h), and purified by HPLC (silica gel, 20-50% EtOAc/hexanes): R$_f$ (0.42, 1:1, hexanes/EtOAc); $^1$H NMR (300 MHz, CDCl$_3$): δ 5.74 (dd, J=6.2, 10.9 Hz, 1H), 5.22-5.06 (m, 1H), 3.73 (s, 3H), 2.83-2.57 (m, 4H), 2.37-2.21 (m, 4H), 2.20-2.12 (m, 4H), 1.92 (dd, J=11.3, 13.1 Hz, 1H), 1.85-1.73 (m, 3H), 1.72-1.54 (m, 2H), 1.47 (s, 3H), 1.12 (s, 3H), 0.99 (t, J=7.4 Hz, 3H); $^{13}$C NMR (75 MHz, CDCl$_3$): δ 201.7, 175.5, 171.4, 170.7, 169.9, 169.3, 74.9, 69.6, 63.9, 53.4, 52.0, 50.8, 42.0, 39.9, 37.9, 35.4, 30.7, 27.8, 20.5, 20.3, 18.1, 16.3, 15.4, 13.6; HRMS-ESI (m/z): [M+H]$^+$ calcd for C$_{24}$H$_{32}$N$_2$O$_8$, 477.2237; found, 477.2218.

Synthesis of Compounds 32a and 32b

Compound 32b (7.9 mg, 15%) was also isolated as a clear resin: R$_f$ 0.62 (1:1, Hexanes/EtOAc); $^1$H NMR (300 MHz, CDCl$_3$): δ 8.14-8.01 (m, 2H), 7.59-7.41 (m, 3H), 5.59 (dd, J=2.0, 12.4 Hz, 1H), 5.23-5.07 (m, 1H), 3.71 (s, 3H), 2.78 (dd, J=6.5, 10.4 Hz, 1H), 2.62 (dd, J=2.3, 15.1 Hz, 1H), 2.52-2.47 (m, 1H), 2.36-2.19 (m, 4H), 2.15 (s, 3H), 1.99 (dd, J=3.0, 13.2 Hz, 1H), 1.95-1.80 (m, 2H), 1.69 (s, 3H), 1.63-1.54 (m, 1H), 1.11 (s, 3H); HRMS-ESI (m/z): [M+H]$^+$ calcd for C$_{27}$H$_{30}$N$_2$O$_8$, 511.2080; found, 511.2059.

Synthesis of Compounds 33a and 33b

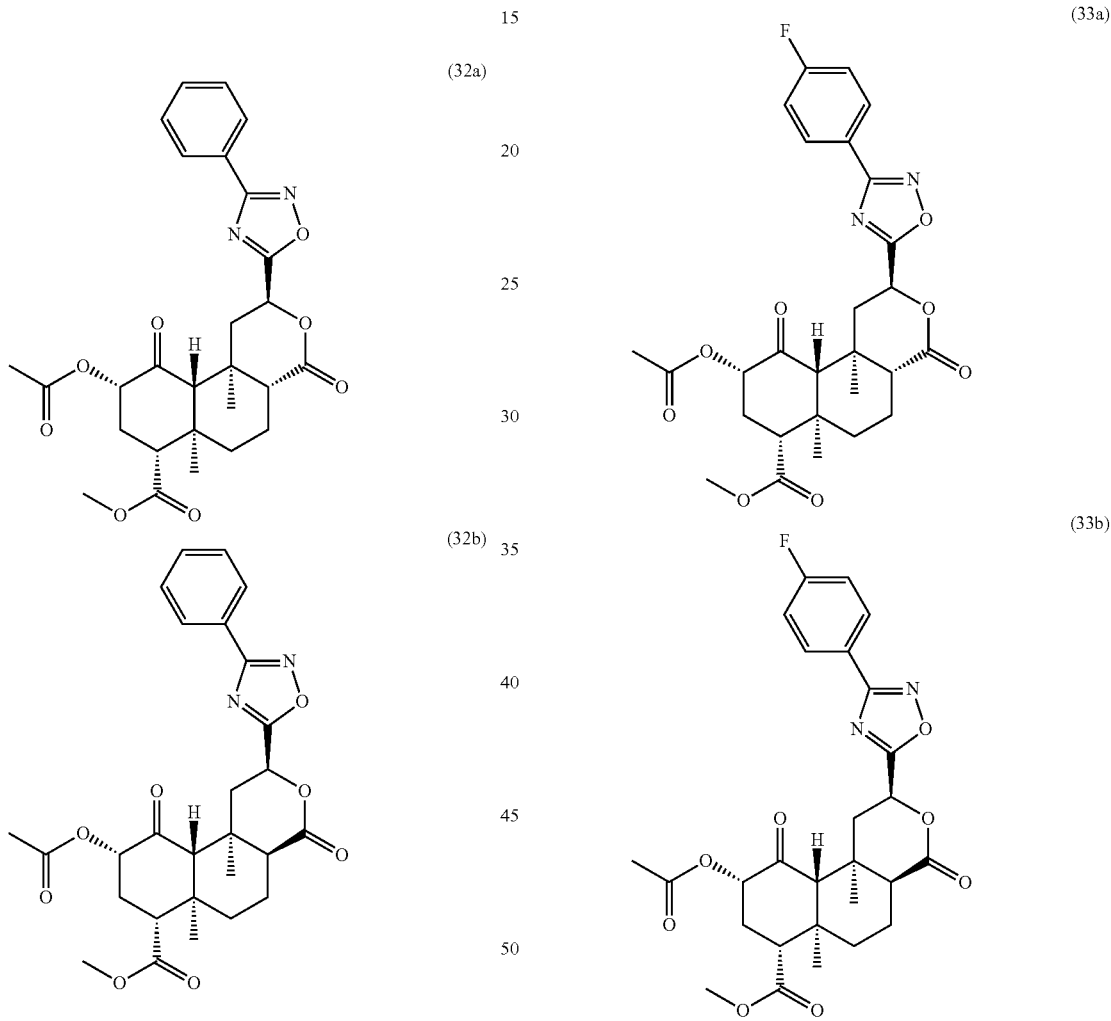

Compound 32a (9.2 mg, 17%) was prepared as a clear resin from 7 (42 mg, 103 µmol), EDCI (27 mg, 140 µmol), HOBt (22 mg, 163 µmol), and benzamidoxime (25 mg, 181 µmol) utilizing the above methodology and stirring at room temperature (22 h), and purified by HPLC (silica gel, 20-25% EtOAc/hexanes): R$_f$ 0.55 (1:1, Hexanes/EtOAc); $^1$H NMR (300 MHz, CDCl$_3$): δ 8.12-8.04 (m, 2H), 7.58-7.44 (m, 3H), 5.83 (dd, J=6.3, 10.8 Hz, 1H), 5.22-5.09 (m, 1H), 3.73 (s, 3H), 2.80-2.67 (m, 2H), 2.37-2.24 (m, 4H), 2.24-2.12 (m, 4H), 2.00 (dd, J=10.5, 12.8 Hz, 1H), 1.86-1.56 (m, 3H), 1.49 (s, 3H), 1.12 (s, 3H); $^{13}$C NMR (75 MHz, CDCl$_3$): δ 201.7, 176.0, 171.4, 169.9, 169.3, 168.6, 131.5, 128.9, 127.5, 126.1, 74.9, 69.7, 63.9, 53.4, 52.0, 50.8, 42.0, 39.9, 37.8, 35.5, 30.7, 20.6, 18.1, 16.3, 15.5; HRMS-ESI (m/z): [M+H]$^+$ calcd for C$_{27}$H$_{30}$N$_2$O$_8$, 511.2080; found, 511.2069.

Compound 33a (3.9 mg, 7%) was prepared as a white powder from 7 (43 mg, 104 µmol), EDCI (27 mg, 140 µmol), HOBt (19 mg, 143 µmol, and 4-fluorobenzamidoxime (23 mg, 150 µmol) utilizing above methodology with stirring at room temperature (2 h), and purified by HPLC (silica gel, 20-25% EtOAc/hexanes): R$_f$ 0.58 (1:1, Hexanes/EtOAc); $^1$H NMR (300 MHz, CDCl$_3$): δ 8.1-8.03 (m, 2H), 7.21-7.13 (m, 2H), 5.82 (dd, J=6.3, 10.9, 1H), 5.21-5.10 (m, 1H), 3.73 (s, 3H), 2.84-2.64 (m, 2H), 2.35-2.25 (m, 4H), 2.22-2.13 (m, 4H), 1.99 (dd, J=11.3, 13.4, 1H), 1.85-1.79 (m, 1H), 1.72-1.56 (m, 2H), 1.50 (s, 3H), 1.13 (s, 3H); $^{13}$C NMR (75 MHz, CDCl$_3$): δ 201.7, 176.1, 171.4, 169.9, 169.2, 167.8, 129.8, 129.7, 116.3, 116.0, 74.9, 69.7, 63.9, 53.5, 52.0, 50.9, 42.0, 40.0, 37.9, 35.5, 30.7, 20.6, 18.1, 16.3, 15.4; HRMS-ESI (m/z): [M+H]+ calcd for $C_{27}H_{29}FN_2O_8$, 529.1986; found, 529.1999.

Compound 33b (9.6 mg, 17%) was also isolated as a white resin: $R_f$ 0.69 (1:1, Hexanes/EtOAc); $^1$H NMR (300 MHz, CDCl$_3$): δ 8.07 (dd, J=5.4, 8.6 Hz, 2H), 7.16 (t, J=8.7 Hz, 2H), 5.57 (dd, J=1.0, 11.9 Hz, 1H), 5.21-5.09 (m, 1H), 3.71 (s, 3H), 2.85-2.69 (m, 1H), 2.60 (dd, J=1.6, 15.1 Hz, 1H), 2.53-2.44 (m, 1H), 2.36-2.19 (m, 4H), 2.15 (s, 3H), 2.03-1.94 (m, 1H), 1.94-1.78 (m, 2H), 1.68 (s, 3H), 1.64-1.52 (m, 1H), 1.10 (s, 3H); HRMS-ESI (m/z): [M+H]+ calcd for $C_{27}H_{29}FN_2O_8$, 529.1986; found, 529.1996.

Synthesis of Compounds 34a and 34b

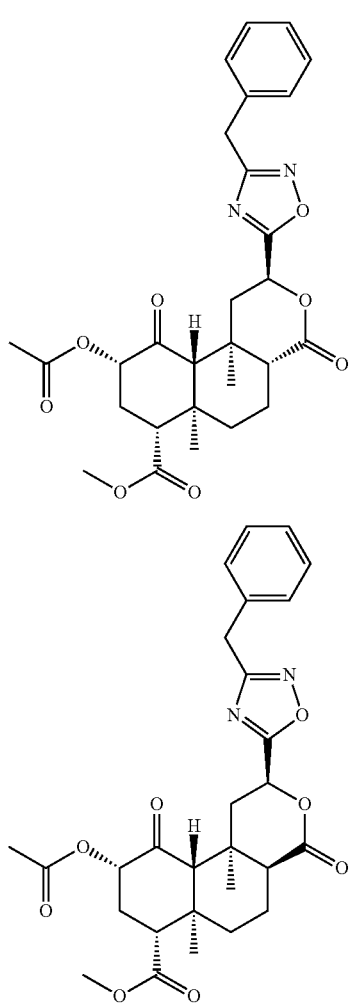

Compound 34a (8.5 mg, 17%) was prepared as a white powder from 7 (39 mg, 95 μmol), EDCI (25 mg, 130 μmol), HOBt (19 mg, 138 μmol), N'-hydroxy-2-phenylethanimidamide (22 mg, 148 μmol) utilizing the above methodology with stirring at room temperature (18 h), and purified by HPLC (silica gel, 20-25% EtOAc/hexanes): $R_f$ 0.50 (1:1, Hexanes/EtOAc); $^1$H NMR (300 MHz, CDCl$_3$): δ 7.37-7.24 (m, 5H), 5.72 (dd, J=6.2, 10.8 Hz, 1H), 5.16-5.07 (m, 1H), 4.08 (s, 2H), 3.73 (s, 3H), 2.77-2.68 (m, 1H), 2.61 (dd, J=6.2, 13.6 Hz, 1H), 2.35-2.24 (m, 2H), 2.23-2.08 (m, 6H), 1.89 (dd, J=10.8, 13.5 Hz, 1H), 1.82-1.74 (m, 1H), 1.70-1.49 (m, 2H), 1.44 (s, 3H), 1.10 (s, 3H); $^{13}$C NMR (75 MHz, CDCl$_3$): δ 201.7, 176.0, 171.4, 169.9, 169.7, 169.3, 134.8, 129.0, 128.8, 127.3, 74.9, 69.6, 63.8, 53.4, 52.0, 50.8, 41.9, 39.8, 37.8, 35.4, 32.2, 30.6, 20.6, 18.0, 16.3, 15.4; HRMS-ESI (m/z): [M+H]+ calcd for $C_{28}H_{32}N_2O_8$, 525.2237; found, 525.2248.

Compound 34b (12 mg, 24%) was also isolated as a clear resin: $R_f$ 0.56 (1:1, Hexanes/EtOAc); $^1$H NMR (300 MHz, CDCl$_3$): δ 7.42-7.25 (m, 5H), 5.48 (dd, J=2.3, 12.2 Hz, 1H), 5.17-5.05 (m, 1H), 4.08 (s, 2H), 3.70 (s, 3H), 2.74 (dd, J=6.4, 10.4 Hz, 1H), 2.50 (dd, J=2.4, 15.1 Hz, 1H), 2.45-2.39 (m, 1H), 2.38-2.11 (m, 7H), 1.95 (dd, J=4.1, 14.1 Hz, 1H), 1.91-1.72 (m, 2H), 1.63 (s, 3H), 1.61-1.52 (m, 1H), 1.08 (s, 3H); (HRMS-ESI (m/z): [M+H]+ calcd for $C_{28}H_{32}N_2O_8$, 525.2237; found, 525.2217.

Example 7

Syntheses of Furan-Substituted Salvinorins (Compounds 2 and 3)

Furan-substituted salvinorins were prepared as described in Scheme 7.

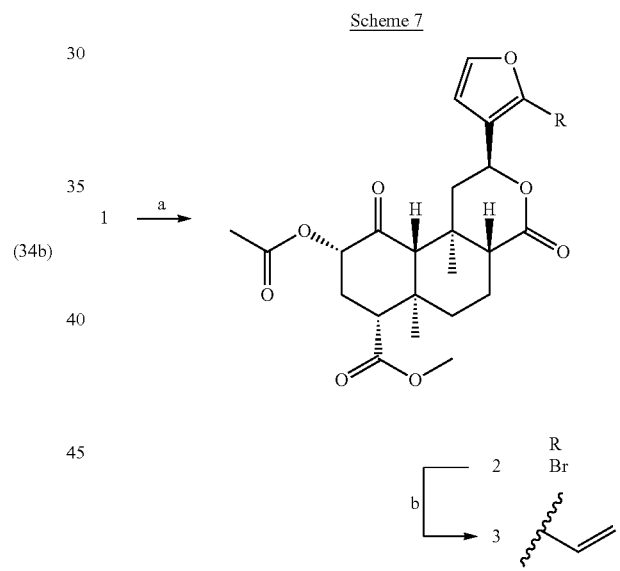

Scheme 7. Syntheses of 16-substituted salvinorin derivatives. Reagents and conditions: (a) NBS, CHCl$_3$, r.t., 10-62%; (b) tributylvinyltin, Pd(PPh$_3$)$_4$, toluene, 80° C., 58%.

We used a modification of the published procedure (Harding et al., *J. Nat. Prod.* 69:107 (2006)) to prepare 16-bromo-salvinorin A (see Scheme 7). The reported conditions (NBS in CH$_3$CN) formed a complex mixture containing only traces of 2. We found that using CHCl$_3$ as solvent was more effective, although the yields were highly variable (10-62%). The highest yield was obtained when the reaction was carried out at room temperature overnight using an old bottle of NBS. Addition of AIBN did not affect the progression of the reaction, and absence of light led to the formation of an unknown side-product. Stille coupling of 2 and tributylvinyltin in the presence of Pd(PPh$_3$)$_4$ provided 3 in 58% yield.

Synthesis of Compound (3)

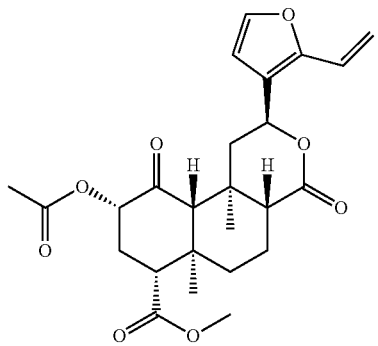

(3)

Tributylvinyltin (5 µL, 18 µmol) was added to a mixture of 2 (8.4 mg, 16 µmol) and Pd(PPh$_3$)$_4$ (catalytic amount) in anhydrous toluene (300 µL) and the reaction was stirred at 80° C. (18 h). A saturated aq KF solution and Et$_2$O were added to the reaction mixture. The organic layer was dried (MgSO$_4$) and the residue purified by column chromatography (silica gel; 0-50% EtOAc/hexanes) to yield 3 (4.4 mg, 58%) as a white powder: R$_f$ 0.32 (1:1, hexanes/EtOAc); $^1$H NMR (300 MHz, CDCl$_3$): δ 7.31 (d, J=1.9 Hz, 1H), 6.53 (dd, J=11.3, 17.3, 1H), 6.33 (d, J=1.9, 1H), 5.71 (dd, J=1.2, 17.3, 1H), 5.57 (dd, J=5.1, 12.0, 1H), 5.25 (dd, J=1.2, 11.3, 1H), 5.17-5.08 (m, 1H), 3.73 (s, 3H), 2.80-2.71 (m, 1H), 2.38 (dd, J=5.1, 13.6, 1H), 2.34-2.24 (m, 3H), 2.23-2.02 (m, 5H), 1.80 (dd, J=2.9, 9.9, 1H), 1.73-1.67 (m, 3H), 1.47 (s, 3H), 1.12 (s, 3H); HRMS-ESI (m/z): [M+H]$^+$ calcd for C$_{25}$H$_{31}$O$_8$: 459.2019; found: 459.2021.

Synthesis of Compound (40)

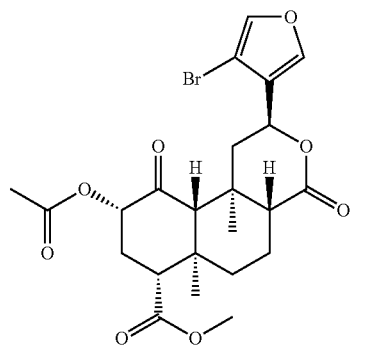

(40)

Salvinorin A (50 mg, 0.12 mmol) was dissolved in AcOH (2.5 mL). To this solution was added NBS (15 mg, 0.13 mmol). The solution was stirred at rt for 16 hours. The mixture was then diluted with CH$_2$Cl$_2$, washed with water, 2M NaOH, and brine, and dried over MgSO$_4$. After evaporation of the solvent, flash chromatography (20% to 80% EtOAc in hexanes) gave bromide 40 as a pale yellow solid. (15 mg, 25% yield); R$_f$ 0.27 (1:1, Hexanes/EtOAc); $^1$H NMR (300 MHz, CDCl$_3$) δ 7.45 (m, 1H), 6.86 (m, 1H), 5.40 (dd, J=5.6, 11.9, 1H), 5.12 (m, 1H), 3.72 (s, 3H), 2.74 (dd, J=5.7, 11.0, 1H), 2.50 (m, 1H), 2.35-2.21 (m, 3H), 2.21-2.11 (m, 5H), 1.79 (m, 1H), 1.69-1.55 (m, 3H), 1.43 (s, 3H), 1.07 (s, 3H). $^{13}$C NMR (75 MHz, CDCl$_3$) δ 202.0, 173.1, 171.8, 170.2, 145.1, 122.2, 121.6, 111.3, 75.2, 70.2, 66.0, 53.6, 52.2, 47.4, 44.6, 42.6, 37.8, 35.4, 30.8, 21.5, 20.8, 18.5, 16.3.

Example 8

In Vitro Binding and Functional Assays

The affinities of compounds 1-3 and 6-34 for opioid receptors were determined by competitive inhibition of [$^3$H]diprenorphine binding to kappa opioid receptors (KOPR), mu opioid receptors (MOPR), and delta opioid receptors (DOPR) in membranes prepared from Chinese hamster ovary cells (CHO) stably transfected with the human KOPR (hKOPR), rat MOPR (rMOPR), and mouse DOPR (mDOPR) as described by Wang et al., J. Pharmacol. Exp. Ther. 312:220 (2005). The rMOPR and the mDOPR have very high sequence homology to the respective human orthologs and share similar binding and functional properties. The potencies and efficacies of compounds 1-3 and 6-34 on hKOPR were determined by their abilities to regulate [$^{35}$S]GTPγS binding to membranes of CHO-hKOPR cells using the approach described by Zhu et al., J. Pharmacol. Exp. Ther. 282:676 (1997). The selective KOPR full agonist, U50, 48814, was used as a reference compound, with its efficacy designated as 100%. Receptor binding and functional assay data were analyzed using Prism (GraphPad Software Inc., San Diego, Calif.). Ki, EC50 (potency) and Emax (efficacy) values were determined using the same software. The in vitro pharmacological data for those derivatives with detectable KOPR binding affinity (Ki<1,000 nM) (1-3, 6-7, 9-11, 13, 16-20) are listed in Table 1. The dose-response curves of compound 6 and U50,488 in the [$^{35}$S]GTPγS functional assay are shown in FIG. 1.

TABLE 1

| Compound tested | | Ki(nM) | EC$_{50}$(nM) | Efficacy[1] |
|---|---|---|---|---|
| 1 | Salvinorin A | 2.53 ± 00.6 | 2.1 ± 0.6 | 105 ± 4 |
| 2 | Compound 2 | 2.9 ± 0.3 | 2.4 ± 0.2 | 108 ± 5 |
| 3 | Compound 3 | 7.1 ± 0.1 | 4.6 ± 0.1 | 120 ± 6 |
| 6 | Compound 6 | 41 ± 5 | 84 ± 8 | 67 ± 5 |
| 7 | Compound 7 | 55 ± 23 | 167 ± 35 | 99 ± 1 |
| 9 | Compound 9 | 498 ± 71 | 330 ± 30 | 98 ± 2 |
| 10 | Compound 10 | 497 ± 13 | >1,000 | — |
| 11 | Compound 11 | 555 ± 97 | 299 ± 13 | 113 ± 3 |
| 13 | Compound 13 | 38 ± 10 | 101 ± 6 | 103 ± 1 |
| 16 | Compound 16 | 83 ± 28 | 195 ± 6 | 103 ± 3 |
| 17 | Compound 17 | 20 ± 2 | 36 ± 5 | 114 ± 4 |
| 18 | Compound 18 | 154 ± 27 | 361 ± 25 | 99 ± 2 |
| 19 | Compound 19 | 196 ± 23 | 508 ± 8 | 94 ± 2 |
| 20 | Compound 20 | 109 ± 12 | 337 ± 54 | 94 ± 2 |
| | U50,488H | 2.2 ± 0.2 | 2.9 ± 0.2 | 100 |

1. Percent of the maximal effect of U50,488H.

Example 9

Modifications at C2

C2 modified salvinorin derivatives can be prepared, for example, from 12-episalvinorin B using the general procedures described below, among others. For example, the stereochemistry at C2 can be inverted using a Mitsunobu reaction (PPh$_3$+DIAD+NuH, where NuH is, for example, an arylalcohol, cyclic imide, or carboxylic acid, among others) (see Scheme 9A). Alternatively; the hydroxy group at C2 can be acylated using an acyl halide or a carboxylic acid and an activating agent (see Scheme 9B); can be alkylated using an alkyl halide (see Scheme 9C); can be converted to a carbamate (see Scheme 9D); or can be converted to an amine (see Scheme 9E). The amine of Scheme 9E can be converted to an amide (see Scheme 9F). These methods can also be used to make analogous modifications at C1, C12, C17, and C4, when these positions are substituted by hydroxyl groups.

Scheme 9A. Nucleophilic Substitution at C(2).

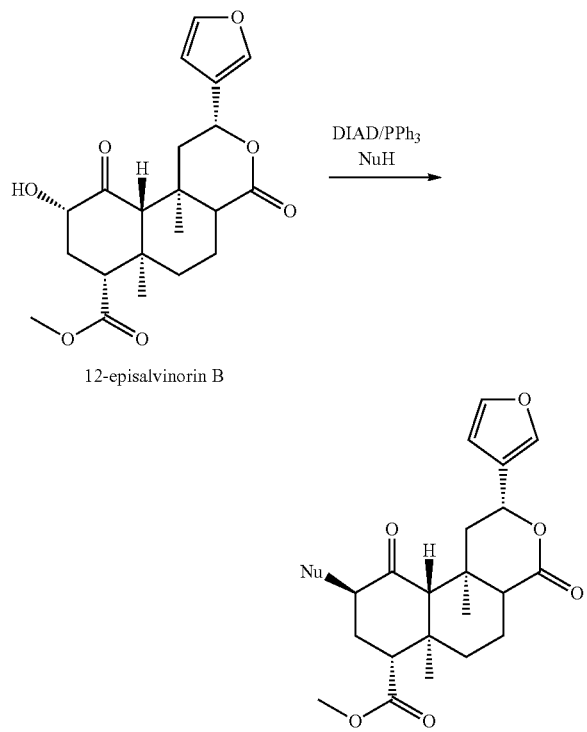

12-episalvinorin B

General Protocol: To a CH$_2$Cl$_2$ solution of 12-episalvinorin B (1 equivalent), triphenylphosphine (3 equivalents), and the nucleophile (3 equivalents) is added diisopropylazodicarboxylate (3 equivalents) (DEAD may also be used) dropwise and the reaction is stirred at room temperature (3.5 hours). Saturated NaHCO$_3$ is added to the reaction mixture. The organic layer is washed with brine, dried (MgSO$_4$), and concentrated in vacuo. The crude material is purified by column chromatography (SiO$_2$; EtOAc-CH$_2$Cl$_2$) to obtain the desired product.

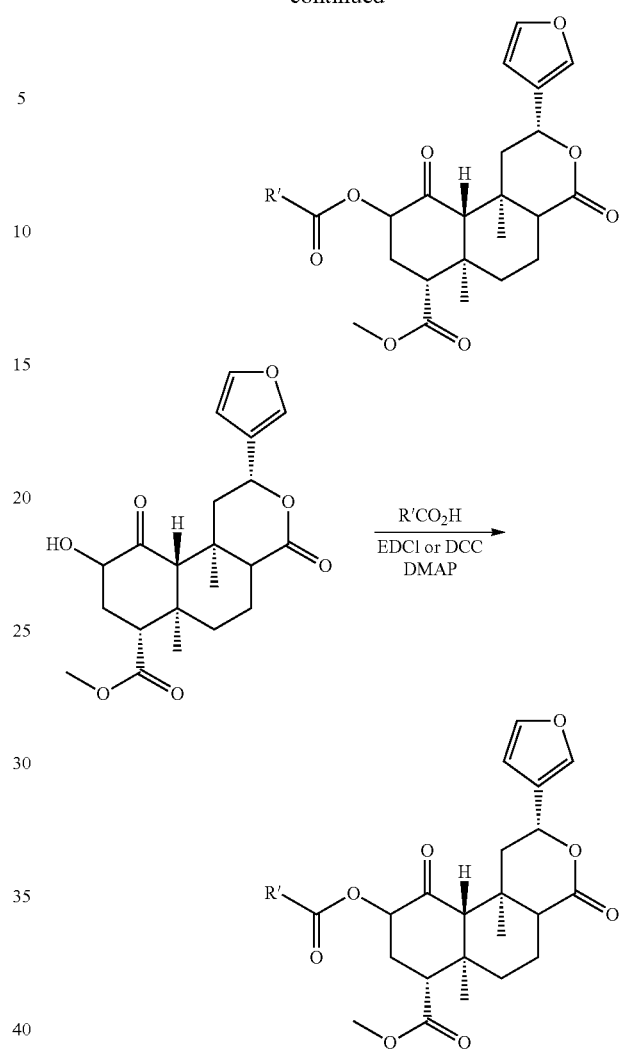

General Protocol: To a pyridine solution of 12-episalvinorin B (1 equivalent) is added the acyl chloride (5 equivalents) and the solution is stirred at room temperature (5 minutes). Ice cold water (2-5 mL) and CH$_2$Cl$_2$ (2-5 mL) are added to the reaction mixture. The organic layer is concentrated in vacuo and then purified by column chromatography (SiO$_2$; EtOAc-hexanes) to obtain the desired product.

Scheme 9B. Synthesis of C(2) esters.

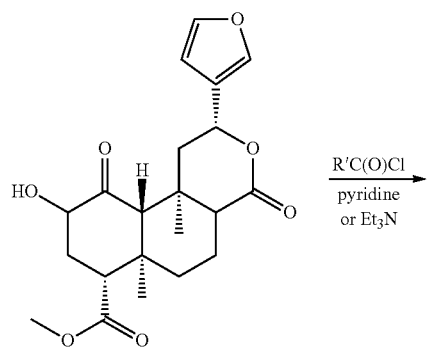

Scheme 9C. Synthesis of C(2) ethers.

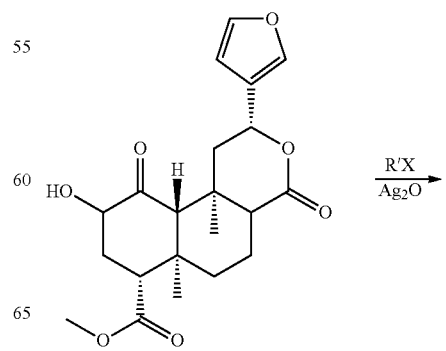

-continued

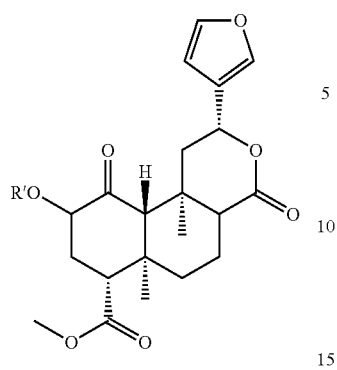

General Protocol: To a stirred MeCN solution of 12-epis-alvinorin B (1 equivalent) is added Ag$_2$O (10 equivalents) and the alkyl halide (20 equivalents). The reaction mixture is concentrated and crude is purified by column chromatography (SiO$_2$; CH$_2$Cl$_2$-EtOAc or EtOAc-hexanes) to obtain the desired product.

-continued

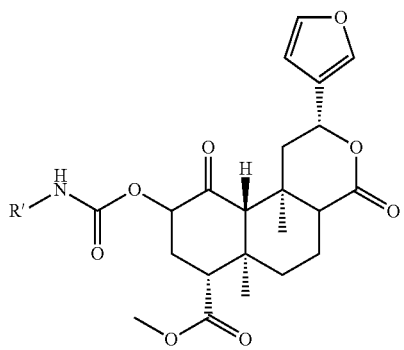

General Protocol: To a cloudy solution of 12-episalvinorin B (1 equivalent) and DMAP (catalytic amount) in pyridine is added the alkyl isocyanate (8-15 equivalents). The reaction mixture is stirred at room temperature (18 hours). The solution is concentrated in vacuo and the residue is purified by column chromatography (SiO$_2$; 1:2, EtOAc:hexanes) to obtain the desired product.

Scheme 9D. Synthesis of C(2) carbamates.

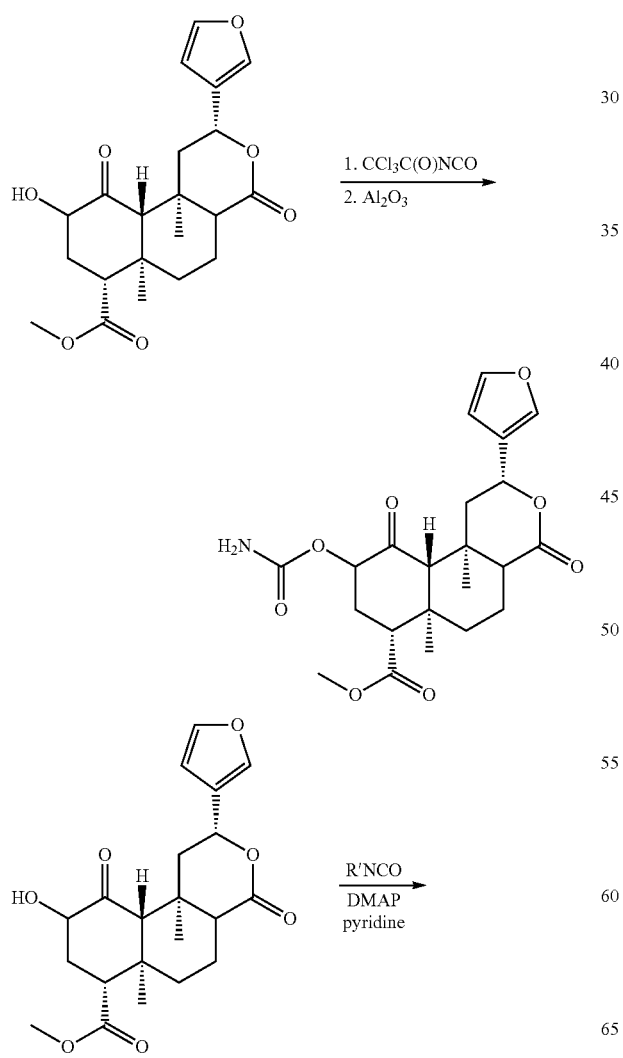

Scheme 9E. Synthesis of C(2) amines.

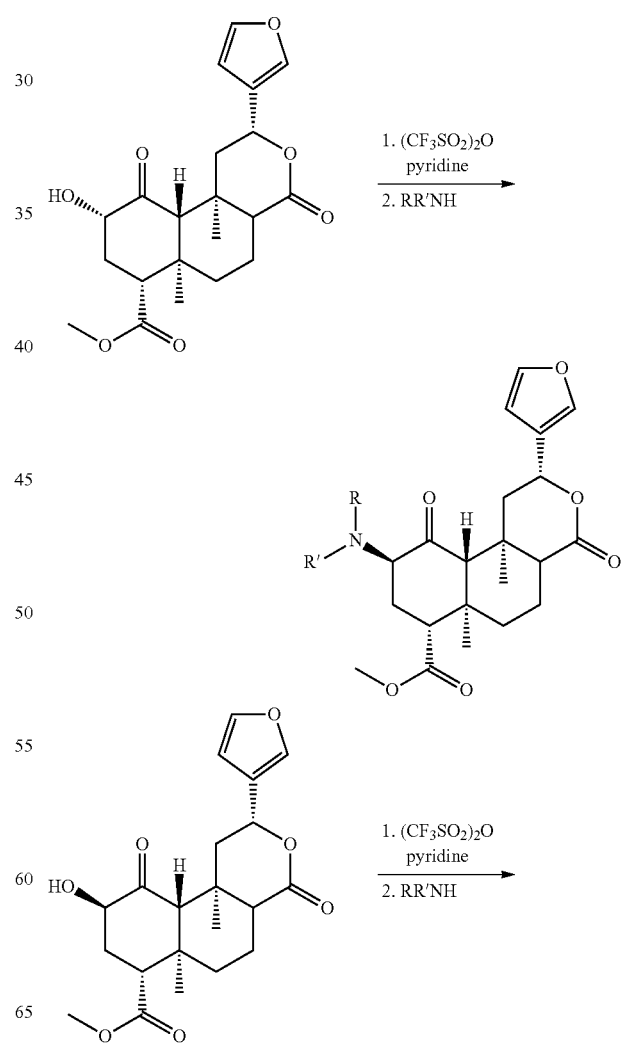

49
-continued

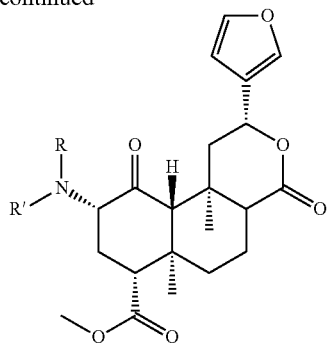

General Protocol: To a cold (0° C.) suspension of 12-episalvinorin B (1 equivalent) in CH$_2$Cl$_2$ is added pyridine (excess) and trifluoromethanesulfonic anhydride (excess) and the reaction solution is stirred at 0° C. for 20 minutes. The reaction solution is washed with 1N HCl (2 mL), brine (2 mL), dried (MgSO$_4$) and evaporated. A solution of the triflate (1 equivalent) in amine (excess) is then stirred at a temperature of between 25° C. and 60° C. for a period of between 1.5 to 18 hours. In select cases CH$_2$Cl$_2$ may be added. The solution is concentrated in vacuo and the residue is purified by column chromatography (SiO$_2$; 9:1, CH$_2$Cl$_2$:EtOAc) to obtain the desired product.

Scheme 9F. Synthesis of C(2) amides.

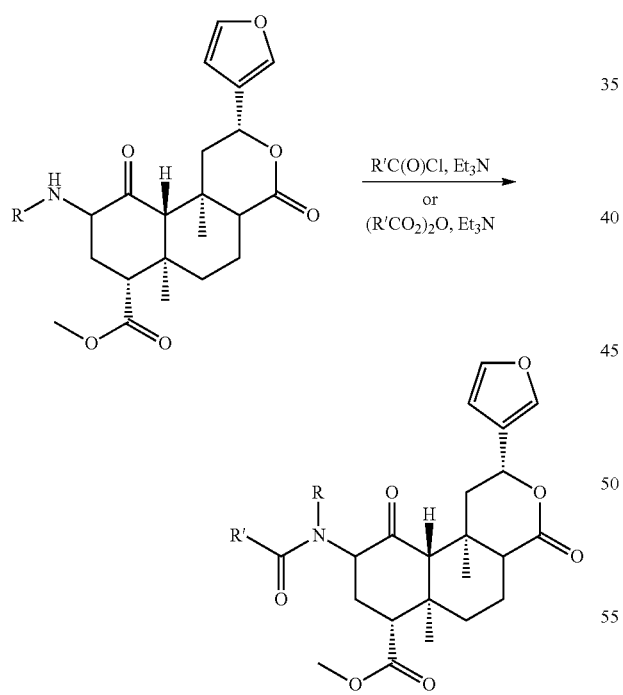

General Protocol: A CH$_2$Cl$_2$ solution of triethylamine (1.25 equivalent) and the acyl chloride or anhydride (1.25 equivalent) is added to the C(2) salvinorin amine (1 equivalent). The reaction solution is stirred at room temperature until completion. The reaction is concentrated and the residue is purified by column chromatography (SiO$_2$; 9:1, CH$_2$Cl$_2$:EtOAc) to obtain the desired product.

50

Example 10

Hydrogenation of the Furan Ring

The furan ring can be hydrogenated using the general procedures shown in Scheme 10, among others. Using H$_2$/Pt/C the furan ring is hydrogenated without disruption of the lactone ring. When more stringent conditions, H$_2$/Pd/C, are employed, the reduction of the furan ring is accompanied by cleavage of the lactone ring and reduction of the C12 position. See Valdes et al., *J. Org. Chem.* 49:4716 (1984); and Koreeda et al., *Chem. Lett.* 2015 (1990).

Scheme 10

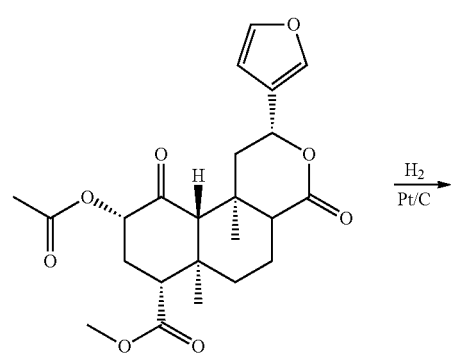

12-episalvinorin A

Example 11

Synthesis of C(4) Derivatives

C4 modified salvinorin derivatives can be prepared, for example, from 12-episalvinorin A using the general procedures shown in Scheme 11, among others. First, the methoxy group is removed using LiI/pyridine. The resulting carboxylic acid group can be converted to an amide using an amine and an activating reagent, or converted to an ester using an alcohol and an activating reagent. The carboxylic acid can be activated, for example, by formation of an active ester, such as nitrophenylesters, N-hydroxysuccinimidyl esters, or others as described in *Chem. Soc. Rev.* 12:129, 1983 and *Angew. Chem. Int. Ed. Engl.* 17:569, 1978. The activated acid can then be reacted with a preselected amine or alcohol to produce the desired amide or ester, respectively.

Scheme 11

12-episalvinorin A

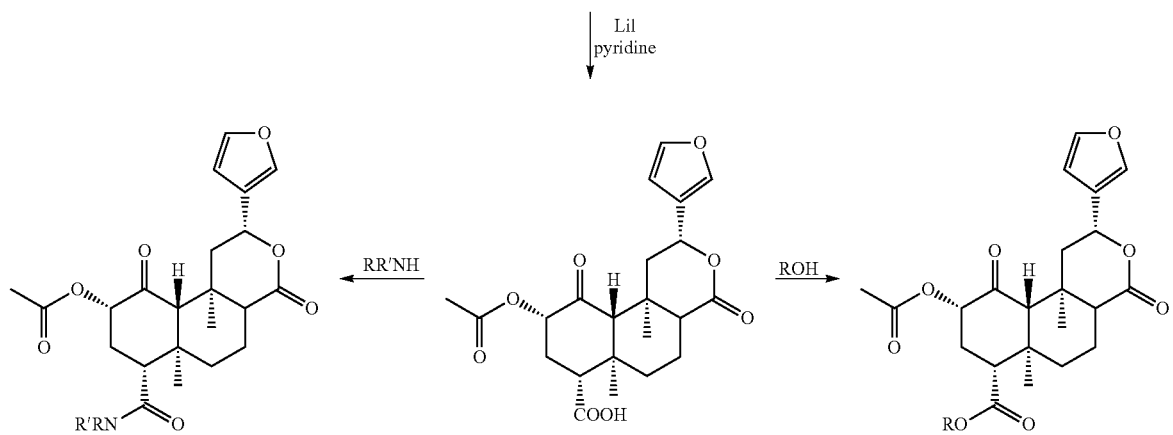

Example 12

Forced Swim Test (FST)

The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile (an indicator of how rapidly the rats "give up" in response to a familiar stressor) are decreased, which is inferred as despair. Standard antidepressants such as desipramine (DMI) and fluoxetine (FLX) extend latencies to become immobile. Drug efficacy in this animal model is predictive of antidepressant efficacy in humans. The FST has been described by Mague et al., *J. Pharmacol. Exp. Ther.* 305:323 (2003).

Figure 3:
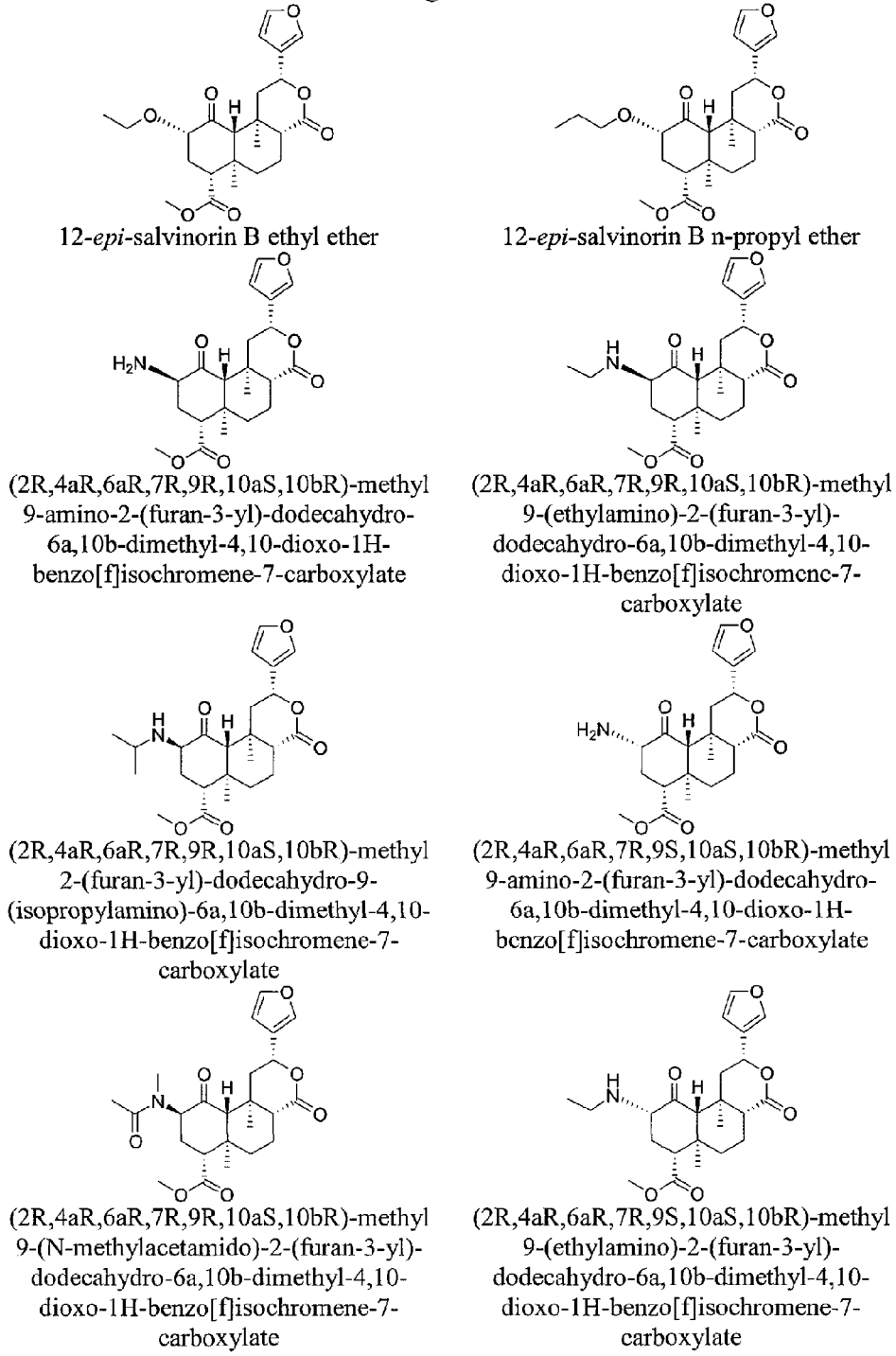
FIG. 3 is a drawing depicting compounds of the invention.

Salvinorin A produces depressive-like effects in the forced swim test in rats without affecting locomotor activity (see FIGS. 3A and 3B).

Example 13

Intracranial Self-Stimulation (ICSS)

Intracranial self-stimulation (ICSS) is highly sensitive to the function of brain reward systems. In this assay, rodents respond to self-administer rewarding electrical stimulation through electrodes implanted within the limbic system. Changes in the rewarding efficacy of the stimulation shift the rate-frequency functions: leftward shifts (reflecting decreases in ICSS thresholds) imply that the stimulation is more rewarding as a result of a treatment, whereas rightward shifts (reflecting increases in thresholds) imply that it is less rewarding. The effects of many types of treatments on ICSS have been described. Most drugs of abuse decrease the amount of stimulation required to sustain responding: this is indicated by leftward shifts in rate-frequency functions and decreased ICSS thresholds. Conversely, agents that block drug reward (dopamine or kappa-opioid receptor agonists) increase the amount of stimulation required to sustain responding: this is indicated by rightward shifts in rate-frequency functions, and increased ICSS thresholds. Thus ICSS is sensitive to manipulations that increase or decrease reward.

Considering that mania is typically associated with increases in reward-driven behavior, the ICSS test may be a reasonable model of mania. Thus drugs that reduce the rewarding effects of the electrical stimulation may have some efficacy in the treatment of mania or related states.

Figure 4:
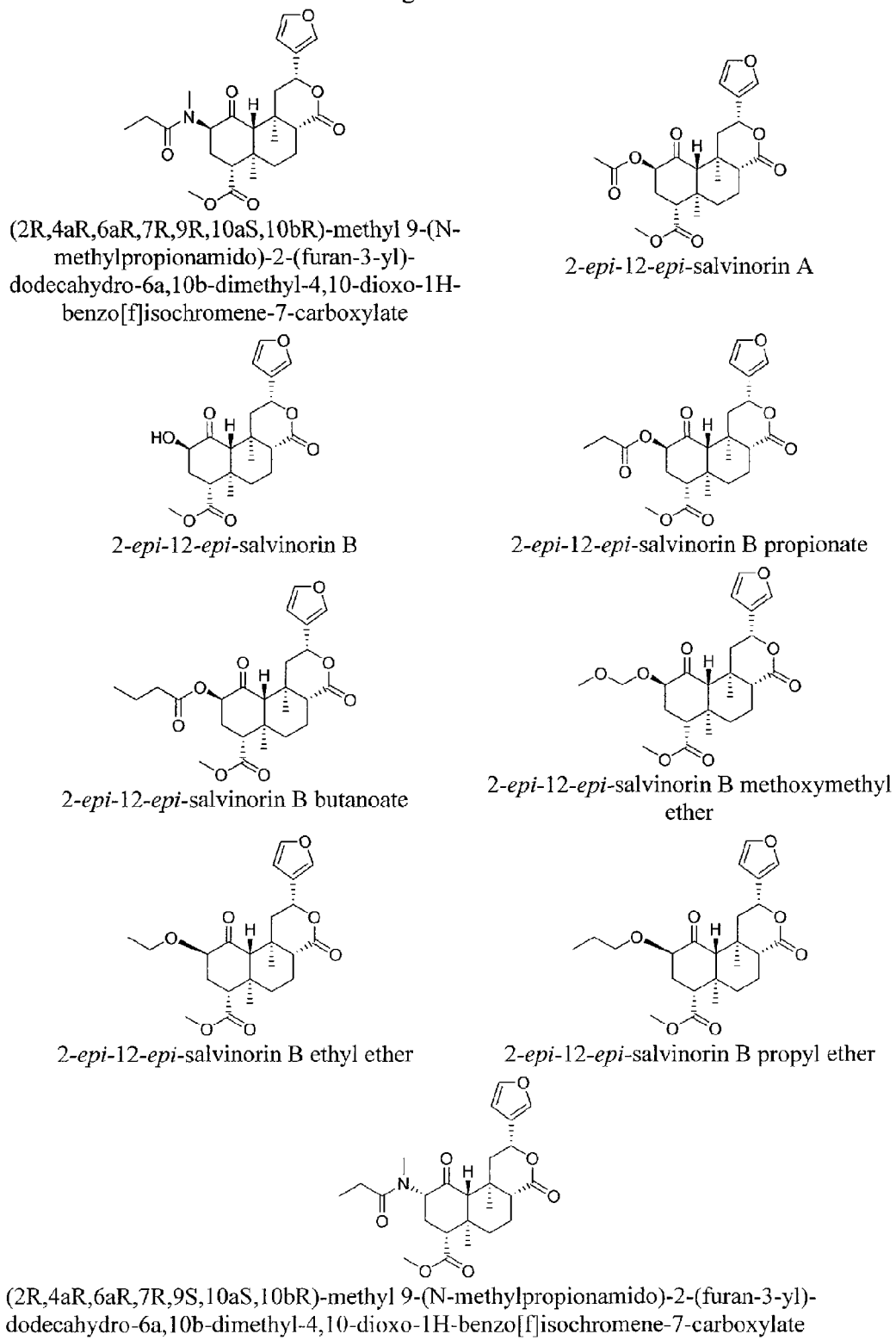
FIG. 4 is a drawing depicting compounds of the invention.
Figure 5:
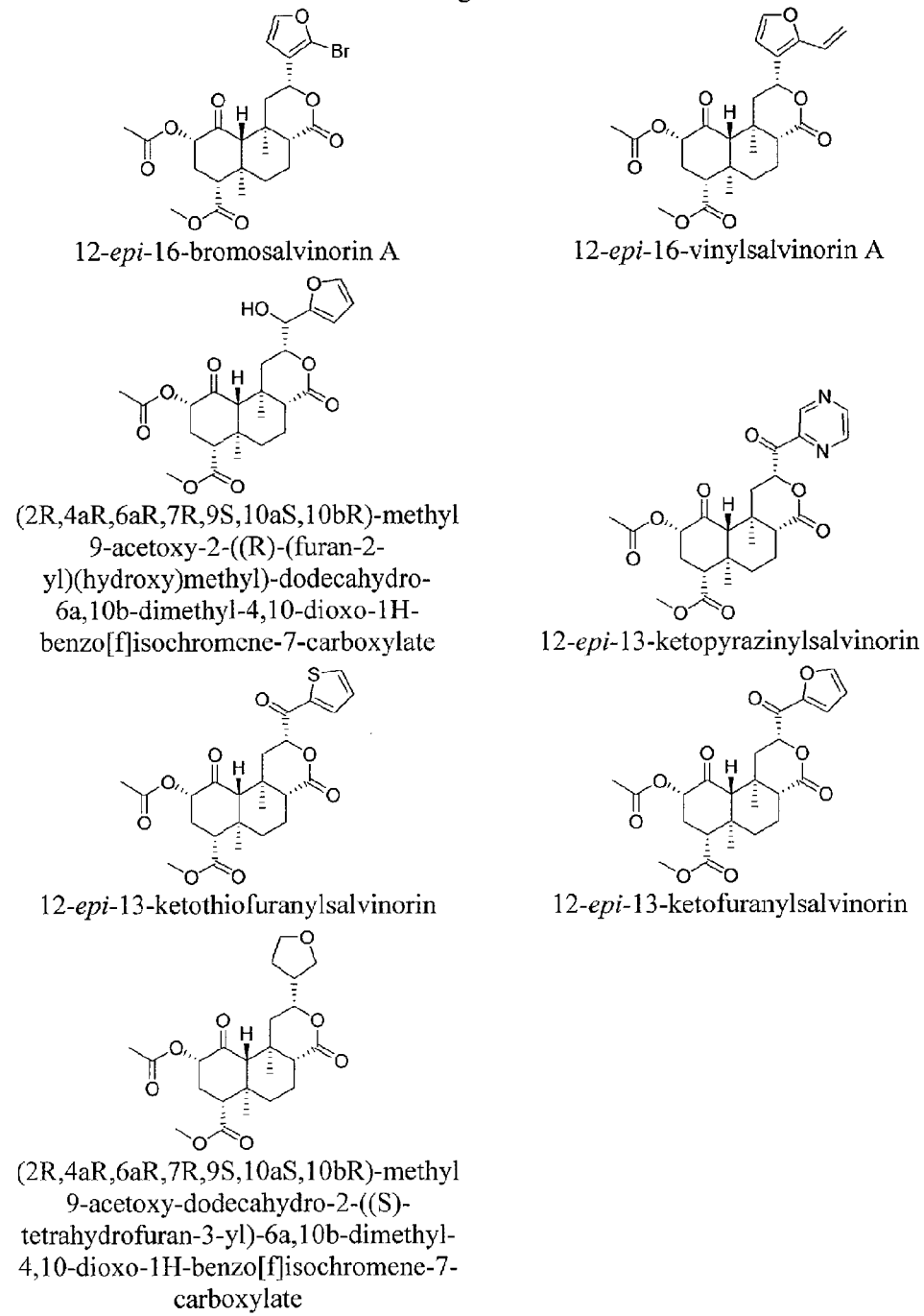
FIG. 5 is a drawing depicting compounds of the invention.

We have found that intraperitoneal administration of 1.0 mg/kg of salvinorin A (a dose with depressive-like effects as demonstrated in the forced swim test (FST) in rats) significantly elevates ICSS thresholds (see FIG. 4). In 1-hour test sessions, injections (1 ml/kg) of 0.9% saline or 70% DMSO (the vehicle for salvinorin A) had no effects on ICSS thresholds, whereas salvinorin A (1.0 mg/kg, IP) significantly elevated ICSS thresholds. Elevations of ICSS thresholds indicate that the lateral hypothalamic brain stimulation is less rewarding as the result of treatment. These findings indicate that salvinorin A in rats causes anhedonia, a hallmark symptom of depressive disorders in humans. Accordingly, kappa agonists may be useful in the treatment of mania and related states in humans.

Example 14

Synthesis of 12-epi-salvinorin B (35)

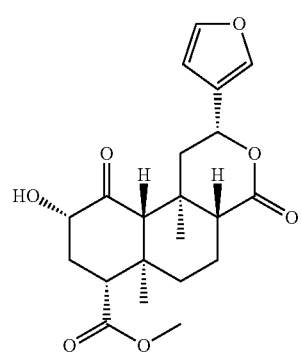

(35)

12-epi-Salvinorin A (52 mg, 0.12 mmol) was dissolved in THF (3 mL) and $H_2O$ (3 mL). To this solution was added $NaHCO_3$ (202 mg, 2.4 mmol), and the reaction was stirred at rt for two hours. The mixture was then diluted with EtOAc, washed with brine, and dried over $MgSO_4$. After evaporation of the solvent, flash chromatography (0% to 5% MeOH in hexanes) gave alcohol 35 as an off-white solid. (27 mg, 58% yield); $R_f$ 0.16 (98:2, $CH_2Cl_2$/MeOH); $^1$H NMR (300 MHz, $CDCl_3$) δ 7.43 (m, 1H), 7.41 (t, J=1.6, 1H), 6.41 (m, 1H), 5.30 (dd, J=6.1, 11.5, 1H), 4.21-3.97 (m, 1H), 3.72 (s, 3H), 2.73 (dd, J=3.1, 13.5, 1H), 2.53-2.41 (m, 3H), 2.34 (dd, J=11.6, 14.6, 1H), 2.18-1.93 (2H), 1.92-1.69 (m, 4H), 1.63 (m, 1H), 1.39 (s, 3H), 1.04 (s, 3H).

Example 15

Synthesis of 2-methoxymethyl ether-12-epi-Salvinorin B (36)

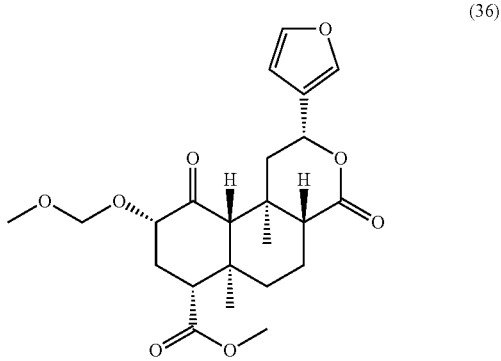
(36)

12-epi-Salvinorin B (11.6 mg, 0.0297 mmol) was dissolved in DMA (500 μL) under argon. To this solution was added NaI (17.8 mg, 0.119 mmol), diisopropylethylamine (28 μL, 0.16 mmol), and MOMCl (11 μL, 0.15 mmol). This solution was warmed to 80° C., and stirred for 18 hours. The mixture was then cooled to rt and diluted with EtOAc, washed with water and brine, and dried over $MgSO_4$. After evaporation of the solvent, flash chromatography (0% to 70% EtOAc in hexanes) gave MOM ether 36 as an off-white solid. (7.7 mg, 60% yield); $R_f$ 0.28 (98:2, $CH_2Cl_2$/MeOH); $^1$H NMR (300 MHz, $CDCl_3$) δ 7.44 (m, 1H), 7.41 (t, J=1.5, 1H), 6.42 (m, 1H), 5.29 (dd, J=6.0, 11.6, 1H), 4.71 (q, J=7.0, 2H), 4.13 (m, 1H), 3.72 (s, 3H), 3.38 (s, 3H), 2.72 (dd, J=3.3, 13.4, 1H), 2.46-2.18 (m, 5H), 2.05-1.68 (m, 4H), 1.58 (m, 1H), 1.39 (s, 3H), 1.06 (s, 3H).

Example 16

Synthesis of 2-ethoxymethyl ether-12-epi-Salvinorin B (37)

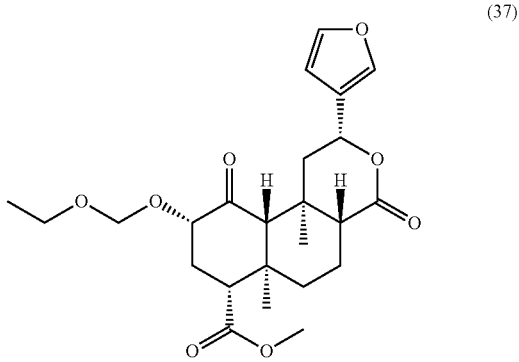
(37)

12-epi-Salvinorin B (15 mg, 0.038 mmol) was dissolved in DMA (500 μL) under argon. To this solution was added NaI (23 mg, 0.15 mmol), diisopropylethylamine (37 μL, 0.21 mmol), and chloromethylethyl ether (16 μL, 0.19 mmol). This solution was warmed to 80° C., and stirred for 18 hours. The mixture was then cooled to rt and diluted with EtOAc, washed with water and brine, and dried over $MgSO_4$. After evaporation of the solvent, flash chromatography (0% to 70% EtOAc in hexanes) gave ethoxymethyl ether 37 as an off-white solid. (11.2 mg, 65% yield); $R_f$ 0.28 (98:2, $CH_2Cl_2$/MeOH); $^1$H NMR (300 MHz, $CDCl_3$) δ 7.43 (m, 1H), 7.40 (t, J=1.7 Hz, 1H), 6.41 (m, 1H), 5.29 (dd, J=6.0, 11.6, 1H), 4.76 (q, J=7.2, 2H), 4.16 (dd, J=7.4, 12.2, 1H), 3.72 (s, 3H), 3.69-3.51 (m, 2H), 2.72 (dd, J=3.3, 13.3, 1H), 2.46-2.27 (m, 4H), 2.20 (m, 1H), 2.05-1.68 (m, 4H), 1.57 (m, 1H), 1.38 (s, 3H), 1.18 (t, J=7.1, 2H), 1.06 (s, 3H).

Example 17

Synthesis of 16-Bromo-12-epi-salvinorin A (38)

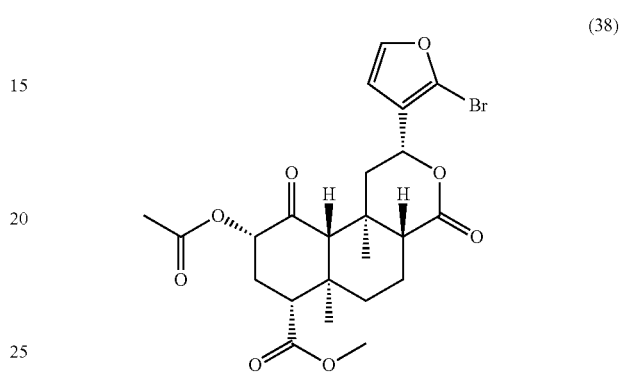
(38)

12-epi-Salvinorin A (20 mg, 0.046 mmol) was dissolved in $CHCl_3$ (500 μL) under argon. To this solution was added NBS (6.0 mg, 0.051 mmol). The solution was stirred at rt for 20 hours. The mixture was then diluted with EtOAc, washed with 2M NaOH, saturated aqueous $NaHCO_3$, and saturated aqueous $Na_2S_2O_3$, and dried over $MgSO_4$. After evaporation of the solvent, flash chromatography (30% EtOAc in hexanes) gave bromide 38 as an off-white solid. (6.5 mg, 28% yield); $R_f$ 0.32 (1:1, Hexanes/EtOAc); $^1$H NMR (300 MHz, $CDCl_3$) δ 7.44 (d, J=1.9, 1H), 6.49 (d, J=2.0, 1H), 5.16 (m, 1H), 3.73 (s, 3H), 2.80 (m, 1H), 2.47 (m, 2H), 2.31 (m, 3H), 2.15 (s, 3H), 2.01-1.54 (m, 6H), 1.43 (s, 3H), 1.07 (s, 3H). $^{13}$C NMR (75 MHz, $CDCl_3$) δ 202.0, 173.1, 171.8, 170.2, 145.1, 122.2, 121.6, 111.3, 75.2, 70.2, 66.0, 53.6, 52.2, 47.4, 44.6, 42.6, 37.8, 35.4, 30.8, 21.5, 20.8, 18.5, 16.3.

Example 18

Synthesis of 13,16-Dibromo-12-epi-salvinorin A (39)

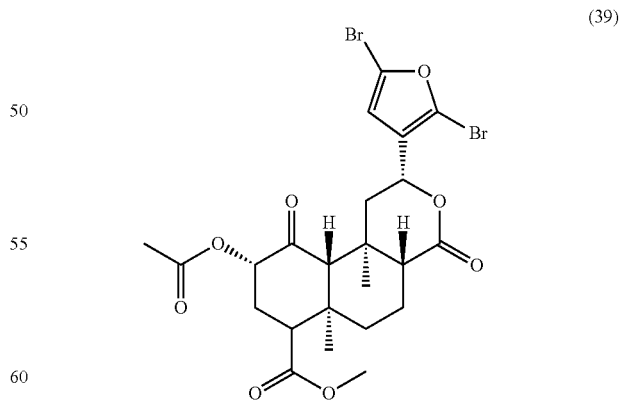
(39)

12-epi-Salvinorin A (20 mg, 0.046 mmol) was dissolved in $CHCl_3$ (500 μL) under argon. To this solution was added NBS (12 mg, 0.10 mmol). The solution was stirred at rt for 20 hours. The mixture was then diluted with EtOAc, washed with 2M NaOH, saturated aqueous $NaHCO_3$, and saturated aqueous $Na_2S_2O_3$, and dried over $MgSO_4$. After evaporation of the solvent, flash chromatography (30% EtOAc in hexanes) gave bisbromide 39 as an off-white solid. (8.5 mg, 31% yield); $R_f$ 0.38 (1:1, Hexanes/EtOAc); $^1$HNMR (300 MHz, CDCl$_3$) δ 6.45 (s, 1H), 5.26-5.07 (m, 2H), 3.73 (s, 3H), 2.79 (m, 1H), 2.44 (m, 2H), 2.36-2.22 (m, 3H), 2.15 (s, 3H), 2.06-1.91 (m, 1H), 1.88-1.50 (m, 5H), 1.39 (s, 3H), 1.07 (s, 3H). $^{13}$C NMR (75 MHz, CDCl$_3$) δ 202.0, 172.7, 171.7, 170.2, 125.4, 123.5, 121.0, 113.0, 75.2, 69.8, 66.0, 53.6, 52.2, 47.4, 44.4, 42.6, 37.8, 35.4, 30.8, 21.4, 20.8, 18.5, 16.3.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:
1. A compound of formula I:

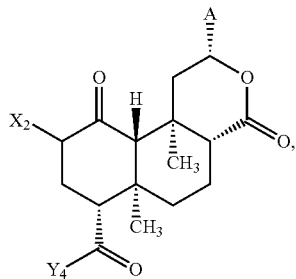

(I)

or a pharmaceutically acceptable salt thereof, wherein
A is selected from $C(O)Y_{13}$, $C(O)X_{13}$, $CH(OR^A)X_{13}$, $CH_2Z_{13}$,

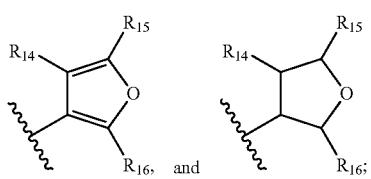

$X_2$ is selected from $OR_2$, O-acyl, $OC(O)Z_2$, $SR_2$, S-acyl, $SC(O)Z_2$, $NR_{21}R_{22}$, $NR_2$-acyl, and $NR_2C(O)Z_2$;
$Z_2$ is $OR_2$, $SR_2$, or $NR_{21}R_{22}$;
$Y_4$ is selected from $OR_4$, $SR_4$, and $NR_{23}R_{24}$;
$X_{13}$ is selected from $C_{2-7}$ heterocyclyl, $C_{6-12}$ aryl, $C_{7-14}$ alkaryl, $C_{3-10}$ alkheterocyclyl, and $C_{1-8}$ heteroalkyl;
$Y_{13}$ is selected from $OR_{13}$, $SR_{13}$, and $NR_{25}R_{26}$;
$Z_{13}$ is selected from O—$R_{13}$, O—$X_{13}$, O-acyl, $OC(O)R_{13}$, S—$R_{13}$, S—$X_{13}$, S-acyl, $SC(O)R_{13}$, $NR_{25}R_{26}$, $NR_{13}$-acyl, NH—$X_{13}$, NHC(O)NH—$R_{13}$, and $NHC(O)OR_{13}$;
each of $R_{14}$, $R_{15}$, and $R_{16}$ is, independently, selected from H, halide, $OR^B$, $C_{1-4}$ alkyl, $C_{2-4}$ alkenyl, $C_{2-4}$ alkynyl; and each of $R^A$, $R^B$, $R_2$, $R_4$, $R_{13}$, $R_{21}$, $R_{22}$, $R_{23}$, $R_{24}$, $R_{25}$, and $R_{26}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{21}$ and $R_{22}$, $R_{23}$ and $R_{24}$, and $R_{25}$ and $R_{26}$, combine to form a heterocyclic ring containing a nitrogen atom.

2. The compound of claim 1, wherein said compound is further described by formula IIa or IIb:

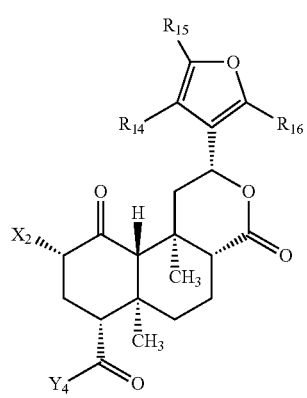

(IIa)

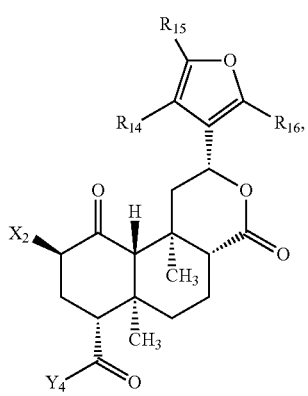

(IIb)

or a pharmaceutically acceptable salt thereof, wherein
$X_2$, $Y_4$, $R_{14}$, $R_{15}$, and $R_{16}$ are as defined in claim 1.

3. The compound of claim 1, wherein said compound is further described by formula IIIa or IIIb:

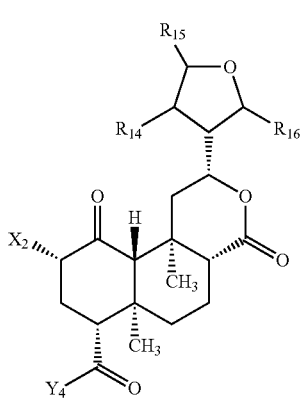

(IIIa)

-continued (IIIb)

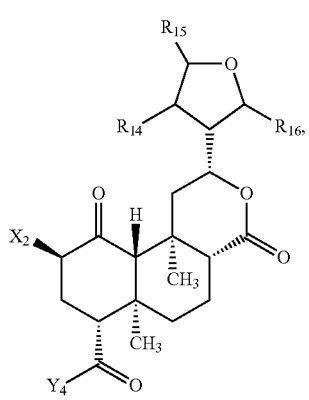

or a pharmaceutically acceptable salt thereof, wherein $X_2$, $Y_4$, $R_{14}$, $R_{15}$, and $R_{16}$ are as defined in claim 1.

4. The compound of claim 1, wherein said compound is further described by formula IVa or IVb:

(IVa)

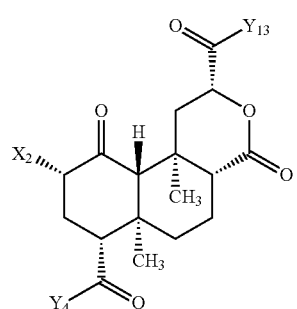

(IVb)

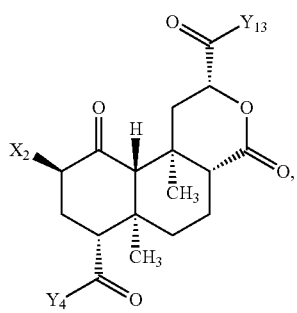

or a pharmaceutically acceptable salt thereof, wherein $X_2$, $Y_4$, and $Y_{13}$ are as defined in claim 1.

5. The compound of claim 1, wherein said compound is further described by formula Va or Vb:

(Va)

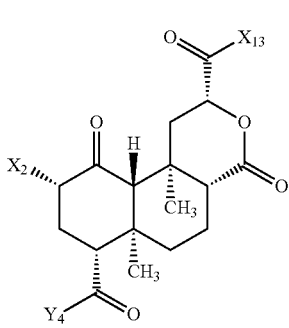

-continued (Vb)

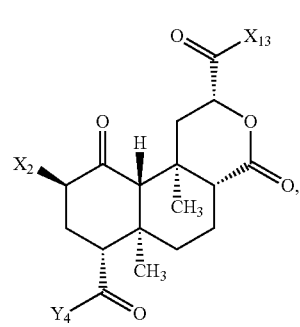

or a pharmaceutically acceptable salt thereof, wherein $X_2$, $Y_4$, and $X_{13}$ are as defined in claim 1.

6. The compound of claim 1, wherein said compound is further described by formula VIa or VIb:

(VIa)

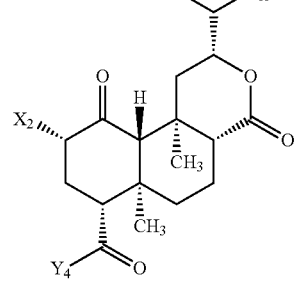

(VIb)

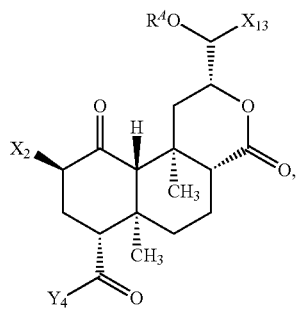

or a pharmaceutically acceptable salt thereof, wherein $X_2$, $Y_4$, $R^A$, and $X_{13}$ are as defined in claim 1.

7. The compound of claim 1, wherein said compound is further described by formula VIIa or VIIb:

(VIIa)

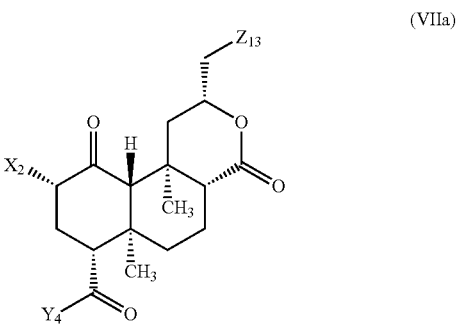

-continued (VIIb)

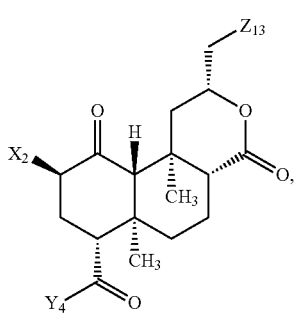

or a pharmaceutically acceptable salt thereof, wherein $X_2$, $Y_4$, and $Z_{13}$ are as defined in claim 1.

8. The compound of claim 1, wherein said compound is further described by formula XI:

(XI)

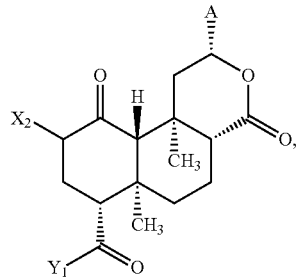

or a pharmaceutically acceptable salt thereof, wherein A is selected from

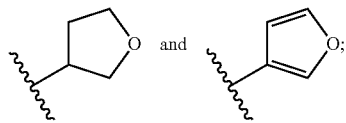 [SMILES: *C1CCOC1 ; "and" ; *c1ccoc1]

$X_2$ is selected from O—$R_2$, O-acyl, OC(O)$Z_2$, S—$R_2$, S-acyl, SC(O)$Z_2$, $NR_{16}R_{17}$, NH-acyl, NHC(O)NH-acyl, and NHC(O)$Z_2$;
$Y_1$ is selected from $OR_{11}$, $SR_{11}$, and $NR_{12}R_{13}$;
$Z_2$ is $OR_2$, $SR_2$, or $NR_{16}R_{17}$; and
each of $R_2$, $R_{11}$, $R_{12}$, $R_{13}$, $R_{16}$, and $R_{17}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{12}$ and $R_{13}$, and $R_{16}$ and $R_{17}$, combine to form a heterocyclic ring containing a nitrogen atom.

9. The compound of claim 8, wherein $Y_1$ is $OCH_3$.

10. The compound of claim 8, wherein said compound is selected from 12-epi-salvinorin A, 12-epi-salvinorin B, 12-epi-salvinorin B propionate, 12-epi-salvinorin B butanoate, 12-epi-salvinorin B methylcarbamate, 12-epi-salvinorin B carbamate ,12-epi-salvinorin B methoxymethyl ether, 12-epi-salvinorin B n-butyl ether, 12-epi-salvinorin B allyl ether, 12-epi-salvinorin B ethyl ether, 12-epi-salvinorin B n-propyl ether, (2R,4aR,6aR,7R,9R,10aS,10bR)-methyl 9-amino-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 9-(ethylamino)-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 2-(furan-3-yl)-dodecahydro-9-(isopropylamino)-6a,10b-dimethyl-4,10-dioxo-1H-benzo[f]isochromene-7-carboxylate, (2R,4aR,6aR,7R,9S,10aS,10bR)-methyl 9-amino-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 9-(N-methylacetamido)-2-(furan-3-yl)-dodecahydro-6a,10b-dimethyl-4,10-dioxo-1H-benzo[f]isochromene-7-carboxylate, (2R,4aR,6aR,7R,9S,10aS,10bR)-methyl 9-(ethylamino)-2-(furan-3-yl)-dodecahydro-6a,10b-dimethyl-4,10-dioxo-1H-benzo[f]isochromene-7-carboxylate, (2R,4aR,6aR,7R,9R,10aS,10bR)-methyl 9-(N-methylpropionamido)-2-(furan-3-yl)-dodecahydro-6a,10b-dimethyl-4,10-dioxo-1H-benzo[f]isochromene-7-carboxylate, 2-epi-12-epi-salvinorin A, 2-epi-12-epi-salvinorin B, 2-epi-12-epi-salvinorin B propionate, 2-epi-12-epi-salvinorin B butanoate, 2-epi-12-epi-salvinorin B methoxymethyl ether, 2-epi-12-epi-salvinorin B ethyl ether, 2-epi-12-epi-salvinorin B propyl ether, (2R,4aR,6aR,7R,9S,10aS,10bR)-methyl 9-(N-methylpropionamido)-2-(furan-3-yl)-dodecahydro-6a,10b-dimethyl-4,10-dioxo-1H-benzo[f]isochromene-7-carboxylate, 12-epi-16-bromosalvinorin A, 12-epi-16-vinylsalvinorin A, (2R,4aR,6aR,7R,9S,10aS,10bR)-methyl 9-acetoxy-2-(R)-(furan-2-yl)(hydroxy)methyl)-dodecahydro-6a,10b-dimethyl-4,10-dioxo-1H-benzo[f]isochromene-7-carboxylate, 12-epi-13-ketopyrazinylsalvinorin, 12-epi-13-ketothiofuranylsalvinorin, 12-epi-13-ketofuranylsalvinorin, and (2R,4aR,6aR,7R,9S,10aS,10bR)-methyl 9-acetoxy-dodecahydro-2-((S)-tetrahydrofuran-3-yl)-6a,10b-dimethyl-4,10-dioxo-1H-benzo[f]isochromene-7-carboxylate, and pharmaceutically acceptable salts thereof.

11. The compound of claim 2, wherein $Y_4$ is $OCH_3$; $X_2$ is $OCH_2OCH_3$; $R_{14}$ and $R_{15}$ are H; and $R_{16}$ is fluorine or iodine.

12. The compound of claim 10, wherein said compound is 12-epi-salvinorin A, or a pharmaceutically acceptable salt thereof.

* * * * *